United States Patent
Ganiger et al.

(10) Patent No.: US 11,999,363 B2
(45) Date of Patent: Jun. 4, 2024

(54) METHODS AND APPARATUS FOR DETECTING FUEL IN OIL, LUBE DEGRADATION, AND FOB THRU OPTICAL AND COLOR CHARACTERIZATION

(71) Applicant: General Electric Company, Schenectady, NY (US)

(72) Inventors: Ravindra Ganiger, Bengaluru (IN); Thomas D. Woodrow, Evendale, OH (US); Anand M S, Bengaluru (IN); Gopi Chandran, Bengaluru (IN); Subasree Ramamoorthy, Bengaluru (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 654 days.

(21) Appl. No.: 17/093,051

(22) Filed: Nov. 9, 2020

(65) Prior Publication Data
US 2021/0139040 A1 May 13, 2021

(30) Foreign Application Priority Data
Nov. 12, 2019 (IN) .............................. 201911045937

(51) Int. Cl.
*G06T 7/90* (2017.01)
*B60W 50/02* (2012.01)
(Continued)

(52) U.S. Cl.
CPC ..... *B60W 50/0205* (2013.01); *F16H 57/0405* (2013.01); *G06N 20/00* (2019.01);
(Continued)

(58) Field of Classification Search
CPC ........ G01N 21/25; G01N 33/30; G01N 21/78; G01N 21/80; G01N 2021/7759;
(Continued)

(56) References Cited

U.S. PATENT DOCUMENTS

| 4,203,725 A | 5/1980 | Snowden, Jr. et al. |
| 5,979,226 A | 11/1999 | Cavestri et al. |

(Continued)

FOREIGN PATENT DOCUMENTS

| CN | 107817244 A | 3/2018 |
| JP | 2010133788 A | 6/2010 |

(Continued)

*Primary Examiner* — Maurice C Smith
(74) *Attorney, Agent, or Firm* — Venable LLP; Kurt W. R. Bessel; Michele V. Frank

(57) ABSTRACT

Systems and techniques that facilitate detecting fuel in oil, lube degradation, and foreign object contamination through optical and/or color characterization are provided. A signature component can generate a digital signature corresponding to a lubricant in a lubrication circuit of an engine. The digital signature can be based on optical or visual properties of a sensor array coupled to the lubrication circuit and exposed to the lubricant, wherein the optical or visual properties of the sensor array can depend on a health of the lubricant. An analysis component can characterize the health of the lubricant by comparing, via a machine learning algorithm, the digital signature with a baseline digital signature corresponding to a desired health-level of the lubricant. In some embodiments, a light emitter component can emit a first light onto the sensor array, and a light receiver component can receive a second light emitted by the sensor array in response to the first light. The signature component can then generate the digital signature based on the first light and the second light. In some embodiments, an image capture component can capture an image of the sensor array. The signature component can then generate the digital signature based on the captured image.

20 Claims, 20 Drawing Sheets

(51) Int. Cl.
  *F16H 57/04* (2010.01)
  *G06N 20/00* (2019.01)
  *G06T 7/00* (2017.01)

(52) U.S. Cl.
  CPC .............. *G06T 7/0002* (2013.01); *G06T 7/90* (2017.01); *B60W 2050/021* (2013.01); *B60W 2050/0215* (2013.01)

(58) Field of Classification Search
  CPC ........ G01N 2021/7786; F16H 57/0405; G06T 2207/20084; G06N 20/00
  See application file for complete search history.

(56) References Cited

U.S. PATENT DOCUMENTS

| | | | |
|---|---|---|---|
| 5,982,847 A * | 11/1999 | Nelson | ................. G01N 23/221 378/45 |
| 7,581,434 B1 | 9/2009 | Discenzo et al. | |
| 7,612,874 B2 | 11/2009 | Kong et al. | |
| 8,676,436 B2 | 3/2014 | Raimarckers et al. | |
| 8,689,601 B2 | 4/2014 | Allam | |
| 9,702,862 B2 | 7/2017 | Hedges | |
| 9,714,931 B2 | 7/2017 | Prabhu et al. | |
| 10,208,638 B2 | 2/2019 | Wada et al. | |
| 10,254,270 B2 | 4/2019 | Potyrailo et al. | |
| 10,317,388 B2 * | 6/2019 | Hegazi | ...................... G01J 3/46 |
| 10,704,734 B2 | 7/2020 | Ganiger et al. | |
| 2005/0227369 A1 | 10/2005 | Richardson et al. | |
| 2013/0250281 A1 * | 9/2013 | Shirata | ................... G01N 21/94 356/70 |
| 2014/0343786 A1 * | 11/2014 | Dvorak | ................ F01M 11/10 702/50 |
| 2017/0307584 A1 | 10/2017 | Hegazi et al. | |
| 2018/0017541 A1 | 1/2018 | Kinard | |
| 2019/0033220 A1 | 1/2019 | Staats et al. | |

FOREIGN PATENT DOCUMENTS

| | | |
|---|---|---|
| JP | 2011231725 A | 11/2011 |
| JP | 2017215253 A | 12/2017 |
| KR | 20120005637 U | 8/2012 |
| KR | 101899139 B1 | 9/2018 |

* cited by examiner

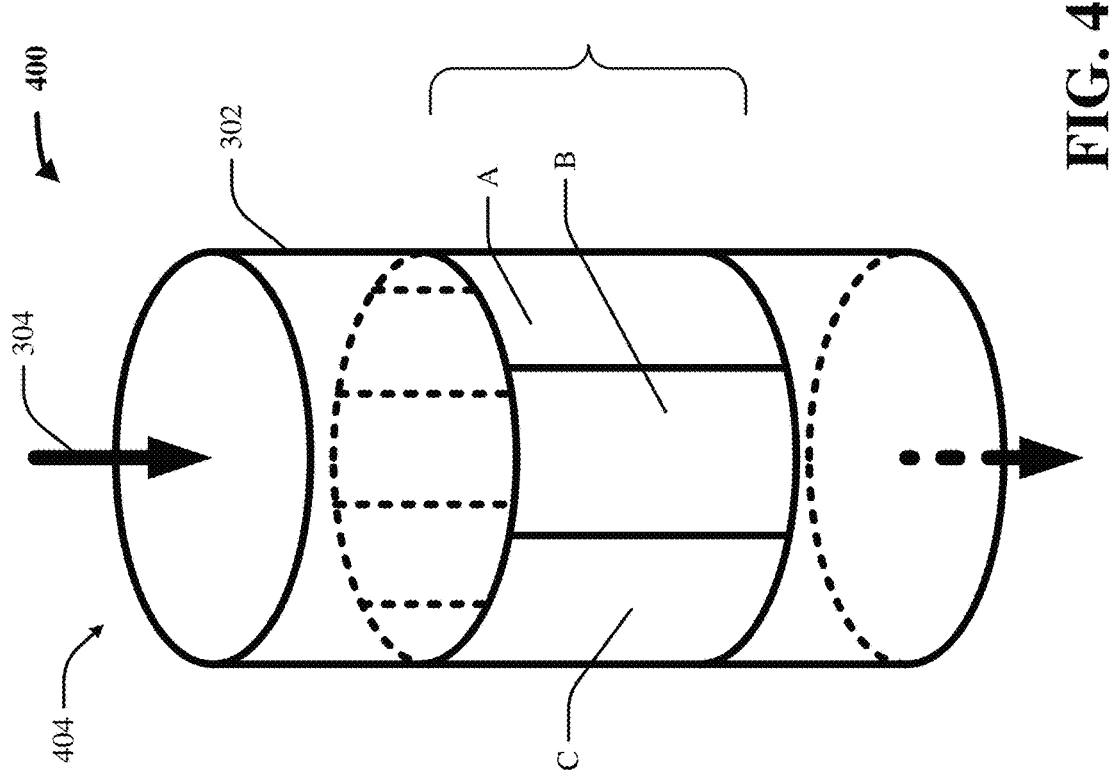
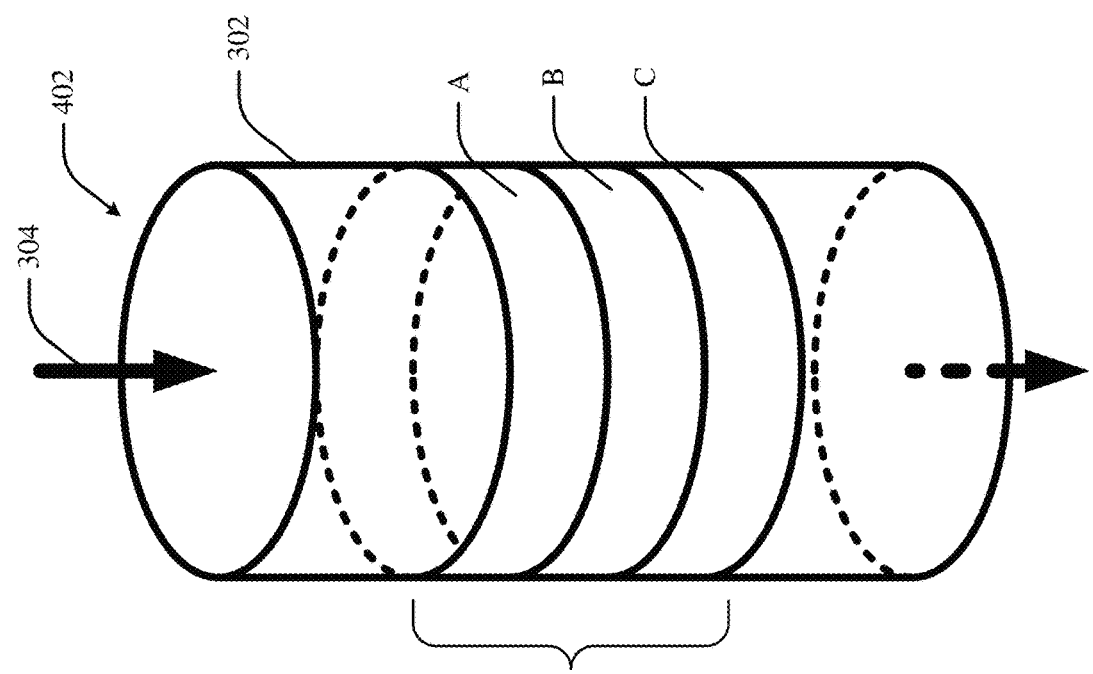
FIG. 4

METHODS AND APPARATUS FOR DETECTING FUEL IN OIL, LUBE DEGRADATION, AND FOB THRU OPTICAL AND COLOR CHARACTERIZATION

CROSS-REFERENCE TO RELATED APPLICATIONS

This application claims priority to Indian Patent Application No. 201911045937, filed on Nov. 12, 2019, entitled "METHODS AND APPARATUS FOR DETECTING FUEL IN OIL, LUBE DEGRADATION, AND FOB THRU OPTICAL AND COLOR CHARACTERIZATION." The entirety of the aforementioned application is incorporated by reference herein

BACKGROUND

The subject disclosure relates generally to engine oil diagnostics, and more particularly to systems and computer-implemented methods that can dynamically detect fuel in oil, lube degradation, and foreign object contamination through optical and color characterization at varying fluid velocities within operating range of turbo machinery.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate detection of fuel in oil, lube degradation, and foreign object contamination through optical and/or color characterization are described.

According to one or more embodiments, a system is provided. The system can comprise a memory that can store computer-executable components. The system can further comprise a processor that can be operably coupled to the memory and that can execute the computer-executable components stored in the memory. In various embodiments, the computer-executable components can comprise a signature component, which can generate a digital signature corresponding to a lubricant in a lubrication circuit of an engine. In various instances, the digital signature can be based on optical or visual properties of a sensor array that can be coupled to the lubrication circuit and exposed to the lubricant. In various aspects, the optical or visual properties of the sensor array can depend on a health of the lubricant (e.g., on identities of one or more contaminants in the lubricant, on concentrations of one or more contaminants in the lubricant, on a deterioration level of the lubricant, and so on). In various embodiments, the computer-executable components can comprise an analysis component, which can characterize the health of the lubricant by comparing, via a machine learning algorithm, the digital signature with a baseline digital signature. In various instances, the baseline digital signature can correspond to a desired health-level of the lubricant (e.g., proper health of the lubricant). In various embodiments, the computer-executable components can comprise a light emitter component and a light receiver component. The light emitter component can emit a first light onto the sensor array, and the light receiver component can receive a second light emitted by the sensor array in response to the first light. In various cases, the signature component can generate the digital signature by determining, based on the first light and the second light, at least one from a group consisting of light absorbance, light reflectance, light fluorescence, light scattering, and light interference of the sensor array. In various embodiments, the computer-executable component can comprise an image capture component, which can capture an image of the sensor array. The signature component can then generate the digital signature based on the image. In various cases, the image can include a first color pattern of the sensor array corresponding to an identity of a contaminant in the lubricant. In various cases, the image can include a second color pattern of the sensor array corresponding to a concentration of the contaminant in the lubricant.

According to one or more embodiments, the above-described system can be implemented as a computer-implemented method.

According to one or more embodiments, the above-described system can be implemented as a computer program product for facilitating detection of fuel in oil, lube degradation, and foreign object contamination through optical and/or color characterization, the computer program product comprising a computer readable memory having program instructions embodied therewith, the program instructions executable by a processing component to cause the processing component to perform various acts.

DESCRIPTION OF THE DRAWINGS

FIG. 4 illustrates a high-level schematic diagram of an example, non-limiting configuration of a sensor array that facilitates detection of fuel in oil, lube degradation, and foreign object contamination through optical characterization in accordance with one or more embodiments described herein.

DETAILED DESCRIPTION

Figure 1:
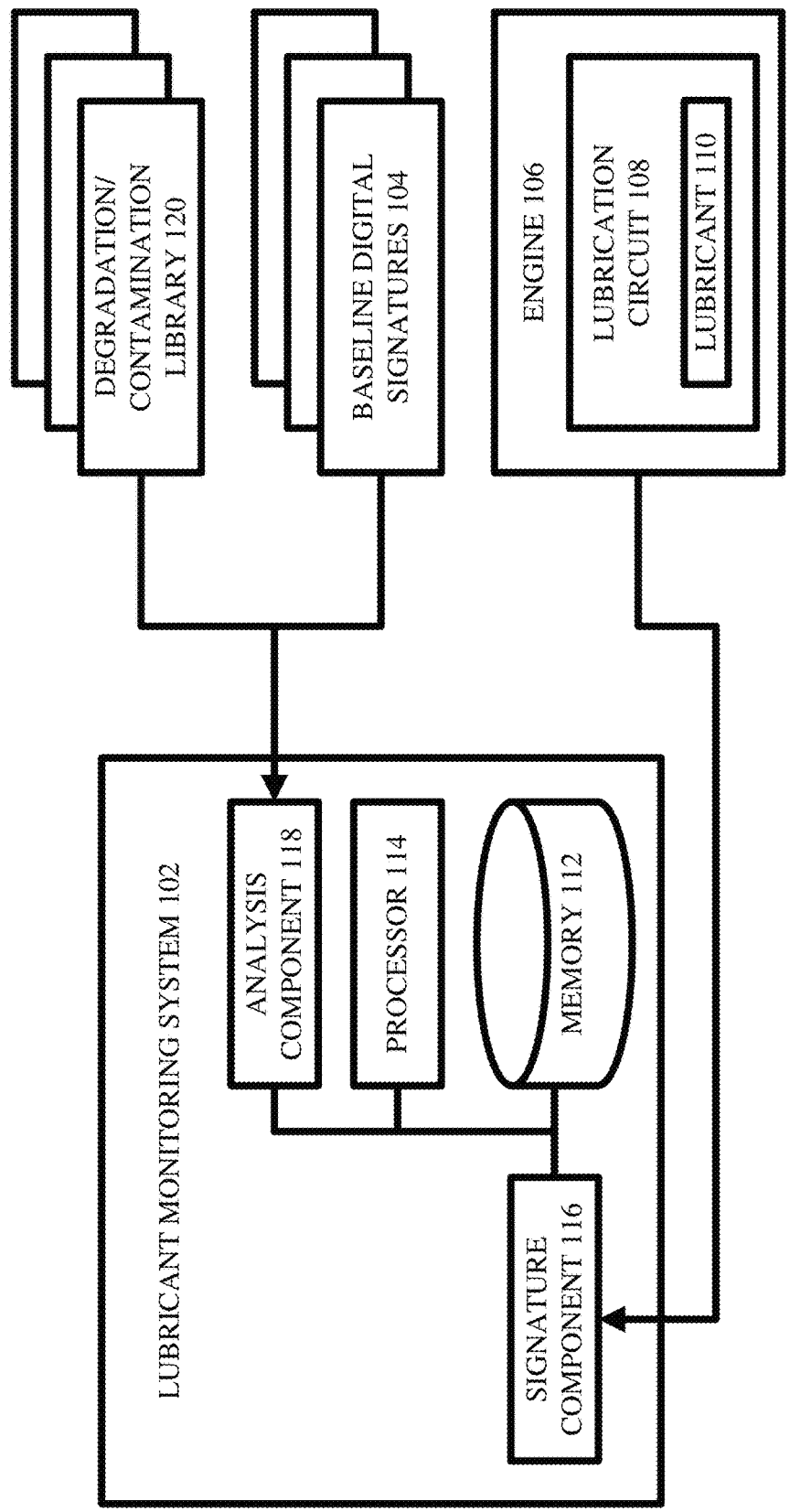
FIG. 1 illustrates a block diagram of an example, non-limiting system that facilitates detection of a source of fuel in oil, lube degradation, and foreign object contamination through optical and/or color characterization at multiple locations in the system and comparison of variations in output in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Modern engines, whether diesel, internal combustion, gas turbine, and so on, utilize during their operation one or more lubricant systems (e.g., engine oil circuits) for temperature control (e.g., cooling) and lubrication (e.g., to reduce frictional wear of internal components). Over time, the lubricant can degrade to varying degrees due to oxidation and/or thermal/compressive deterioration, can develop varying levels of slag, varnish, and/or coking due to excessive temperatures, can experience consumption/depletion of necessary additives, and/or can become contaminated with varying concentrations of fuel, moisture, chemicals, other foreign objects, and so on. Such degradation and/or contamination can reduce the effectiveness of the lubricant, can clog or otherwise damage one or more portions of the engine, and can pose significant safety hazards (e.g., portions of fuel mixed in an oil circuit can ignite during operation, causing an engine fire). Particularly in the aerospace field, degradation and/or contamination of aircraft engine lubricant can result in in-flight-shut-down (IFSD), which can cause catastrophic accidents and loss of life. Thus, systems and/or methods for monitoring and detecting in real-time lubricant degradation and/or contamination are advantageous. Moreover, such systems and/or methods which can output comprehensive compositional analyses of the lubricant and determine and/or suggest one or more portions of a lubrication circuit in need of repair and/or inspection are even more advantageous.

A lubricant (e.g., oil) in a lubrication circuit (e.g., oil flow system) of an engine can experience different types and/or severities of deterioration, degradation, and/or contamination. For example, a lubricant can develop varnish of varying thickness (e.g., a thin film of lubricant attached to an inner surface area of a channel or tank in a lubrication circuit), slag/sludge of varying densities (e.g., congealed lubricant that can clog channels or tanks in the lubrication circuit), coking of varying severities (e.g., solidified lubricant that can clog channels or tanks in the lubrication circuit), fuel contamination of varying concentration (e.g., fuel leaking into the lubrication circuit), moisture contamination of varying concentration (e.g., water/coolant leaking into the lubrication circuit), chemical contaminations of varying concentrations (e.g., oxides, sulphides, silicates, metallics, nitrides, phenolics, esters, amines, aromatics, and so on being introduced into the lubrication circuit), foreign object contamination of varying concentration (e.g., dust, dirt, debris, and so on introduced into the lubrication circuit), and so on. Generally, lubricant is periodically changed in order to avoid such deterioration and/or contamination. However, such periodic maintenance may not always be performed (e.g., based upon cost, present need, desired workload of the engine or the lubricant, desire to maximize useful life of the engine or the lubricant while minimizing costs, and so on).

In the absence of periodic maintenance, the lubricant should be monitored to ensure that excessive deterioration and/or contamination is avoided. Existing lubricant monitoring systems and/or techniques generally employ offline maintenance and offline diagnosis (e.g., oil samples from an aircraft are collected and examined in a laboratory through chemical analysis, infrared spectroscopy, viscosity analysis, human olfactory analysis, and so on). Such systems/techniques are suboptimal because they are not performed in real-time during operation of the engine. Although some automated systems and/or techniques exist that offer real-time in situ monitoring of engine lubricant, they are generally limited to detecting lubricant temperature, lubricant pressure, or only specific chemical reagents that may be present in a lubricant (e.g., metallic ions representing only a small subset of potential contaminants). Moreover, such automated systems/techniques do not fully determine the instantaneous composition of the lubricant or provide a comprehensive characterization of the health of a lubricant. Instead, such automated systems/techniques generally provide only a binary output/alert to an operator of the engine (e.g., contamination or no contamination, deterioration or no deterioration, and so on). Furthermore, such existing systems/techniques generally provide only a single and/or global determination of lubricant health that applies to the entire lubricant (e.g., they determine that the entire lubricant is either contaminated or not) rather than more granularly determining the composition and/or health of the lubricant at one or more specific points along the lubrication circuit. This is because existing systems/techniques generally assume that the lubricant is homogenous and ignore the possibility of the lubricant having a heterogeneous composition and/or otherwise not being uniformly mixed throughout the circuit (e.g., the lubricant may have higher and/or lower concentrations of contaminants at various locations along a flow path of the lubrication circuit and/or along a cross-section perpendicular to the flow path, may have slag and/or coke at some locations and not others, and so on) Thus, such automated systems/techniques do not determine and/or suggest specifically where in the lubrication circuit a certain contaminant was likely introduced or otherwise determine and/or suggest a specific portion of the lubrication circuit that requires inspection and/or repair. Further still, such existing systems/techniques do not employ machine learning algorithms to learn baseline characteristics of a healthy lubricant or to learn from mistaken diagnoses made by the system but proven incorrect via manual inspection. Finally, such existing systems/techniques provide monitoring/diagnostics only to a single engine, rather than to a fleet of engines having similarly-designed lubrication circuits and lubricants, and thus such systems/techniques do not allow an entire fleet of engines to simultaneously learn from the lubrication diagnostic errors of a single engine.

Various embodiments described herein include systems, computer-implemented methods, apparatus, and/or computer program products that facilitate detection of fuel in oil, lube degradation, and foreign object contamination through optical and/or color characterization. In one or more instances, the subject claimed innovation can use changes in optical and/or color properties exhibited by chemoresistors (also called chemiresistors) on a sensor array coupled to a lubrication circuit and exposed to a lubricant in order to characterize a health of the lubricant (e.g., deterioration/degradation level, contaminant identity, contaminant concentration, and so on). In various cases, the subject claimed innovation can leverage machine learning and/or pattern recognition, trained via supervised learning, to compare current and baseline optical properties of the sensor array (e.g., fluorescence intensity, reflectance intensity, absorbance intensity, scatter intensity, interference intensity, and so on exhibited by chemo-responsive optical coatings arranged on the sensor array) and/or to compare current and baseline color properties of the sensor array (e.g., color patterns exhibited by chemo-responsive and/or pH indicator dyes arranged on the sensor array), where the optical properties and/or color properties of the sensor arrays can depend on the health/composition of the lubricant. Based on these comparisons, the subject claimed innovation can generate one or more values (e.g., scalars, vectors, matrices, and so on) that correspond to a comprehensive health and/or composition of the lubricant at the location of the sensor array (e.g., one or more of the scalars or one or more elements of the vectors/matrices can represent levels of degradation/oxidation of the lubricant at that location, can represent levels of additive depletion in the lubricant at that location, can represent identities of specific contaminants in the lubricant at that location, can represent concentrations of specific contaminants in the lubricant at that location, can represent identities and/or concentrations of desired and/or required chemicals at that location, and so on). In various cases, the subject claimed innovation can employ a plurality of sensor arrays positioned at a plurality of locations/points along the lubrication circuit, with each sensor array providing a comprehensive health/composition diagnosis of the lubricant at its corresponding location/point. Thus, various embodiments of the subject claimed innovation can granularly determine the health and/or composition of the lubricant at various locations in the lubrication circuit, which healths and/or compositions may not be homogenous. Moreover, various embodiments can determine where in the lubrication circuit a specific contaminant was likely introduced (e.g., if fuel is detected in the lubrication circuit, embodiments of the subject claimed innovation can determine a specific channel, pipe, tank, and/or manifold of the lubrication circuit through which the fuel contamination was likely first introduced into the lubrication circuit, based on the location of the sensor array that is first in time to detect the contaminant). In various instances, the subject claimed innovation can employ a digital twin component that digitally models the monitored lubrication circuit and which can apply self-learning algorithms (e.g., learn from diagnoses that are proven incorrect through manual inspection). In various instances, the digital twin component can be communicatively connected to a fleet of engines, such that the lubricant diagnostic results of a single engine in the fleet can be used to simultaneously and/or instantaneously teach the entire fleet.

Various embodiments of the subject innovation can be employed to use hardware and/or software to solve problems that are highly technical in nature (e.g., to facilitate the automated detection, prediction, and/or categorization of deterioration and/or contamination of engine lubricant), that are not abstract and that cannot be performed as a set of mental acts by a human. Further, some of the processes performed can be performed by a specialized computer for carrying out defined tasks related to engine lubricant diagnostics (e.g., generation of a digital signature corresponding to a lubricant in a lubrication circuit of an engine, the digital signature being based on optical or visual properties exhibited by chemo-responsive and/or photo-responsive coatings and/or dyes of a sensor array coupled to the lubrication circuit and exposed to the lubricant; characterizing the health of the lubricant by comparing, via a machine learning algorithm, the digital signature to a baseline digital signature corresponding to proper health of the lubricant; emitting a first light onto the sensor array and receiving a second light emitted by the sensor array in response to the first light, wherein the digital signature is generated based on the first and second lights; capturing an image of the sensor array, wherein the digital signature is generated based on first and second color patterns exhibited by the sensor array in the image; and so on). In various aspects, the subject claimed innovation can provide technical improvements to the field of engine lube diagnostics, by utilizing optical and/or color characterization in conjunction with machine learning and/or pattern recognition to determine the real-time health and/or composition of a lubricant at one or more locations along a lubrication circuit, to identify real-time deterioration and/or contamination levels of the lubricant, to estimate where in the lubrication circuit such contamination was first introduced, and to learn from mistaken diagnoses and/or determinations. Such lube diagnostic systems can result in improved lube diagnostic efficacy, increased lubricant durability, improved performance retention of the engine, reduced unplanned engine removals, and better engine fleet management, and thus constitutes a concrete and tangible technical improvement in the prior art.

FIG. 1 illustrates a block diagram of an example, non-limiting system 100 that can facilitate detection of fuel in oil, lube degradation, and foreign object contamination through optical and/or color characterization in accordance with one or more embodiments described herein. As shown, a lubricant monitoring system 102 can leverage baseline digital signatures 104 in order to diagnose and/or characterize the health and/or composition of a lubricant 110 flowing through a lubrication circuit 108 of an engine 106. In various embodiments, the engine 106 can be any suitable type of engine (e.g., internal combustion engine of an automobile, diesel engine of an automobile, gas turbine engine of an aircraft, an engine of any other type of vehicle such as landcraft, aircraft, watercraft, or spacecraft, stationary engines, and so on). In various aspects, the lubricant 110 can be any type of suitable engine lubricant (e.g., engine oil) having any suitable viscosity, any suitable density, any suitable SAE and/or API grade, and/or with any other suitable chemical and/or physical properties. In various cases, the lubrication circuit 108 can be any type of suitable hydraulic circuit that facilitates flow of the lubricant 110 through portions of the engine 106 requiring lubrication. In various instances, the lubrication circuit 108 can be any suitable series of lines, pipes, tanks, channels, manifolds, oil pumps, oil filters, oil sumps, oil strainers, oil pressure regulators, oil galleries, oil ducts in an engine crankshaft, oil ducts in an engine camshaft, oil ducts in an engine rotor, oil ducts in engine bearings, and so on.

In various embodiments, the baseline digital signatures 104 can represent baseline data (e.g., baseline optical data exhibited by chemo-responsive optical coatings and/or baseline color data exhibited by chemo-responsive dyes, as described in more detail below) that correspond to a desired health-level of the lubricant 110 (e.g., baseline data that correspond to the lubricant 110 when the lubricant 110 is proper, healthy, uncontaminated, acceptably contaminated, and/or so on). For example, fresh engine oil can, in various embodiments, typically contain approximately 30% alkanes, 50% naphthenes (e.g., a type of cycloalkane), 15% aromatics, and 5% asphaltics. Thus, the baseline digital signatures 104 can include optical and/or color signatures exhibited by sensor arrays that are exposed to the lubricant 110 when the lubricant 110 has the above and/or similar composition. In some instances, when a sensor array displays such baseline digital signatures 104, it can be determined and/or inferred that the lubricant 110 at the sensor array's location has approximately the following composition: 30% alkanes, 50% naphthenes, 15% aromatics, and 5% asphaltics. In various instances, different lubricants can have different healthy compositions and thus can have different baseline digital signatures 104.

In various embodiments, a single lubricant (e.g., lubricant 110) can exhibit different baseline digital signatures 104 depending on measurement location in the lubrication circuit 108 (e.g., the baseline digital signatures 104 can include various baseline signatures corresponding to desired health-levels and/or compositions of the lubricant 110 at various locations along the lubrication circuit 108). For instance, if the lubricant 110 is being monitored at three separate locations along the lubrication circuit 108, then the baseline digital signatures 104 can include three separate baseline signatures, one for each location. In some embodiments, the lubricant 110 can have a same healthy composition and thus a same baseline digital signature at each of those three locations. In some embodiments, the lubricant 110 can have different healthy compositional characteristics and thus different baseline signatures at each of those three locations. In various aspects, the compositional characteristics of the lubricant 110 corresponding to proper health can vary along the path of the lubrication circuit 108 (e.g., oil additives and/or debris can be included at one part of the lubrication circuit 108 and can be consumed/depleted/filtered out at another part of the lubrication circuit 108, and so on). For example, the baseline signature of the lubricant 110 at a particular location in the lubrication circuit 108 can, in some embodiments, correspond to normal and/or acceptable levels of contamination (e.g., engine oil entering a sump and/or a filter can be acceptably contaminated notwithstanding the fact that the oil is healthy and/or fresh, and the oil leaving the filter can be uncontaminated). In other words, healthy lubricant can, in some cases, have non-zero contamination, such as immediately upstream from a filter, and so on.

In various cases, the baseline digital signatures 104 can be derived and/or obtained from development engines that are known to have healthy lubricant (e.g., engines tested under controlled conditions, such as in a laboratory), fielded engines that are known to have healthy lubricant or that were recently serviced (e.g., engines deployed in commercial or private automobiles, aircraft, watercraft, and so on), theoretical performance thresholds (e.g., theoretical properties of a healthy lubricant as determined by a computational and/or analytical model of the lubricant 110), and so on. As explained more fully below, the baseline digital signatures 104 can include any optical signatures and/or color signatures that are associated with chemo-responsive optical coatings and/or color or pH indicator dyes that are configured on a sensor array that is exposed to the lubricant 110 when the lubricant 110 is substantially healthy (e.g., optical output and/or color output of the sensor array when the lubricant 110 is healthy, undegraded, uncontaminated, acceptably contaminated, and so on).

In various embodiments, the lubricant monitoring system 102 can comprise a processor 114 (e.g., computer processing unit, microprocessor, and so on) and a computer-readable memory 112 that is operably and/or operatively and/or communicatively connected/coupled to the processor 114. The memory 112 can store computer-executable instructions which, upon execution by the processor 114, can cause the processor 114 and/or other components of the lubricant monitoring system 102 (e.g., signature component 116, analysis component 118, and so on) to perform one or more acts. In various embodiments, the memory 112 can store computer-executable components (e.g., signature component 116, analysis component 118, and so on), and the processor 114 can execute the computer-executable components.

In various embodiments, the lubricant monitoring system 102 can comprise a signature component 116. The signature component 116 can, in various instances, generate a digital signature of the lubricant 110 at one or more times and/or at one or more locations along the lubrication circuit 108. As explained more fully below, the signature component 116 can, in various embodiments, employ one or more sensor arrays that are coupled to the lubrication circuit 108 such that the sensor arrays are exposed to the lubricant 110.

In various cases, a sensor array can comprise one or more chemo-responsive optical coatings (e.g., carbon nanotube coatings, garnet phosphor coatings with enhanced spectral characteristics, graphite oxide and/or graphene oxide coatings, any other suitable chemoresistor coating, and so on), where the optical behavior of each coating can change and/or depend on the chemical and/or physical interactions that the coating has with the constituents of the lubricant 110. In various aspects, the optical behavior and/or optical properties of a coating can include fluorescence intensity of the coating, reflectance intensity of the coating, absorbance intensity of the coating, scatter intensity of the coating, interference intensity of the coating, any other detectable optical response/characteristic of the coating, and so on. In various aspects, the optical properties of a coating can be measured in one or more of the visible spectrum, the infrared (IR) spectrum, the ultraviolet (UV) spectrum, and so on. In various instances, the optical behavior of a chemo-responsive optical coating can change uniquely depending on the composition/health of the lubricant 110 (e.g., a chemo-responsive optical coating can exhibit a particular set of optical properties when exposed to a healthy portion of the lubricant 110, the coating can exhibit a different set of optical properties when exposed to a slightly deteriorated portion of the lubricant 110 with moderate fuel contamination, the coating can exhibit a still different set of optical properties when exposed to a heavily deteriorated portion of the lubricant 110 with slight moisture contamination, the coating can exhibit yet another different set of optical properties when exposed to certain chemical contaminants in the lubricant 110, and so on). In various cases, the signature component 116 can generate the digital signature corresponding to the lubricant 110 based on the measured optical behaviors/properties of the one or more chemo-responsive optical coatings arranged on the sensor array.

In various cases, a chemo-responsive optical coating can demonstrate high selectivity, and thus can be responsive to only a certain contaminant and/or chemical in the lubricant 110 (e.g., a coating whose optical properties change only when exposed to sulphides in the lubricant 110). In various cases, a coating can demonstrate low selectivity, and thus can be responsive to one or more of a variety of contaminants and/or deterioration levels of the lubricant 110 (e.g., a coating whose optical properties change in same and/or different ways when exposed to at least one of metallics, amines, aromatics, fuel, or moisture in the lubricant 110). In various embodiments, the sensor array can comprise a plurality of chemo-responsive optical coatings, with each coating being responsive to a different contaminant, deterioration aspect, and/or composition aspect of the lubricant 110 (e.g., with some coatings being responsive to metallic contaminants, some coatings being responsive to oxides, some coatings being responsive to alkanes, some coatings being responsive to naphthenes, some coatings being responsive to aromatics, some coatings being responsive to fuel/petroleum, some coatings being responsive to coke, some coatings being responsive to slag, and so on).

As explained more fully below, in various embodiments, a sensor array can instead comprise one or more chemo-responsive color dyes, where the visible color of each dye can change and/or depend on the chemical interactions that the dye has with the constituents of the lubricant 110. In various cases, a chemo-responsive color dye can demonstrate high selectivity, and thus can change color only via chemical interaction with a certain contaminant (e.g., a color dye that reacts only to the presence of silicates in the lubricant 110 and does not react to the presence of other contaminants in the lubricant 110). In various cases, a chemo-responsive color dye can demonstrate low selectivity, and thus can change color via chemical interaction with one or more of a variety of different chemicals (e.g., a color dye that reacts to the presence of at least one of silicates, amines, metallics, fuel, or moisture in the lubricant 110, and so on). In various instances, the color change of such a dye can be different for each contaminant that the dye is designed to detect (e.g., the dye turns a first color when reacting with silicates, a second color when reacting with amines, a third color when reacting with metallics, and/or a combination of colors when simultaneously reacting with more than one of the aforementioned, and so on). In various cases, a plurality of color dyes can be arranged on the sensor array so as to detect a host of different contaminants (e.g., with some dyes being responsive to metallic contaminants, some dyes being responsive to oxides, some dyes being responsive to alkanes, some dyes being responsive to naphthenes, some dyes being responsive to aromatics, some dyes being responsive to fuel/petroleum, some dyes being responsive to coke, and so on). In various aspects, such a sensor array can exhibit a baseline and/or healthy color pattern (e.g., the initial pattern of visible colors exhibited by the arrangement of color dyes on the sensor array prior to exposure to the lubricant 110 and/or during exposure to only a healthy portion of the lubricant 110).

In various embodiments, a sensor array can further comprise one or more pH indicator dyes, which can change visible color and/or shade of visible color based on concentrations of contaminants in the lubricant 110. For instance, a single pH indicator dye can change from a bright red to a progressively darker red as the concentration of a particular contaminant in the lubricant 110 increases. As another example, a single pH indicator dye can change from white to a progressively darker color (e.g., black, brown, red, purple, green, pink, blue, orange, and so on) as the concentration of a particular contaminant in the lubricant 110 increases. In some cases, a pH indicator dye can change from dark to light in color as the concentration of the contaminant it is designed to detect increases. In various aspects, the color gradient exhibited by the pH indicator dye can correspond, and therefore indicate, a particular concentration level of the contaminant that it is designed to detect.

In various embodiments, the chemo-responsive color dyes and the pH indicator dyes arranged on a sensor array can exhibit a particular color pattern when exposed to a healthy portion of the lubricant 110, the dyes can exhibit a different color pattern when exposed to a slightly deteriorated portion of the lubricant 110, the dyes can exhibit a still different color pattern when exposed to a heavily deteriorated portion of the lubricant 110, the dyes can exhibit yet another different color pattern when exposed to certain chemical contaminants in the lubricant 110, and so on. In various instances, the signature component 116 can generate the digital signature corresponding to the lubricant 110 based on the measured color patterns of the one or more chemo-responsive color dyes and/or the one or more pH indicator dyes arranged on the sensor array.

In various embodiments, a sensor array can include any suitable combination of chemo-responsive optical coatings, chemo-responsive color dyes, and/or pH indicator dyes simultaneously.

In various embodiments, the lubricant monitoring system 102 can comprise an analysis component 118. In various aspects, the analysis component 118 can receive the one or more digital signatures generated by the signature component 116 and compare them with the baseline digital signatures 104 in order to detect changes in the digital signatures of the lubricant 110. Based on these changes in digital signatures, the analysis component 118 can comprehensively characterize/classify the health and/or the composition of the lubricant 110 at the one or more locations of the one or more sensor arrays of the signature component 116 (e.g., a determined change in digital signature at a particular sensor array location of the lubrication circuit 108 can correspond to a particular health-level and/or a particular composition of the lubricant 110 at that location).

In various instances, the analysis component 118 can perform such comparison and characterization/classification by employing a trained machine learning algorithm (e.g., a neural network). In various embodiments, the analysis component 118 can generate, via the trained machine learning algorithm, one or more normalized parameters based on the digital signature created by the signature component 116, with the normalized parameters indicating health and/or composition of the lubricant 110. In various cases, the machine learning algorithm of the analysis component 118 can be trained using a degradation/contamination library 120. In various aspects, the degradation/contamination library 120 can include measured digital signatures (e.g., measured optical properties of chemo-responsive optical coatings, and/or measured color patterns of chemo-responsive color dyes and pH indicator dyes) that correspond to known deterioration levels, known contamination levels, and/or known compositions of the lubricant 110.

For example, in embodiments that rely primarily on chemo-responsive optical coatings, the degradation/contamination library 120 can include a first optical digital signature that corresponds to sensor array output at a particular location in the lubrication circuit 108 where the lubricant 110 was known to have light coking and moderate deterioration, can include a second optical signature that corresponds to sensor array output at that location when the lubricant 110 was known to have little deterioration but high nitride and ester contamination, can include a third optical signature that corresponds to sensor array output at that location when the lubricant 110 was known to have heavy slag, moderate fuel contamination, and low moisture contamination, and so on. As another example, in embodiments that rely primarily on chemo-responsive color dyes and pH indicator dyes, the degradation/contamination library 120 can include a first color signature that corresponds to sensor array output at a particular location in the lubrication circuit 108 where the lubricant 110 was known to have light varnish and high aromatics, a second color signature that corresponds to sensor array output at that location when the lubricant 110 was known to have high moisture and low amine contamination, a third color signature that corresponds to sensor array output at that location when the lubricant 110 was known to have high fuel contamination and heavy coking, and so on.

In various cases, the degradation/contamination library 120 can be leveraged to perform supervised training, and/or any other type of learning such as unsupervised training or reinforcement learning, of the analysis component 118, such that the analysis component 118 can take as input the detected digital signatures generated by the signature component 116 and the baseline digital signatures 104 and produce as output a comprehensive characterization and/or classification of the health and/or composition of the lubricant 110 at locations corresponding to the sensor arrays of the signature component 116 (e.g., the analysis component 118 can substantially determine the chemical composition of the lubricant 110 including contaminants at various locations along the lubrication circuit 108, can substantially determine the concentrations of the contaminants at those locations, can substantially determine a deterioration level of the lubricant 110 at those locations, and so on, by learning how the sensor array properties change in response to various healths/compositions of the lubricant 110). In various embodiments, similar to the baseline digital signatures 104, the degradation/contamination library 120 can be derived from development engines with known suboptimal health-levels and/or known suboptimal compositions of the lubricant 110, fielded engines with known suboptimal health-levels and/or known suboptimal compositions of the lubricant 110, theoretical models of the lubricant 110, and so on.

In various instances, the analysis component 118 can determine a segment and/or section of the lubrication circuit 108 that can need repair and/or inspection, based on the output of a plurality of sensor arrays. For instance, if the lubricant monitoring system 102 employs multiple separate sensor arrays located at different points along the lubrication circuit 108, then the location in the lubrication circuit 108 corresponding to any sensor array that detects an anomalous composition and/or health of the lubricant 110 can be determined to require repair and/or inspection. In various embodiments, if a particular sensor array is the first in time to detect contamination, the analysis component 118 can determine that an inspection and/or repair should be conducted on the channels, pipes, and/or components of the lubrication circuit 108 that are located immediately upstream from the particular sensor array (e.g., between the triggered sensor array and the closest upstream sensor array that was not triggered). In this way, embodiments of the subject claimed innovation can determine/infer which specific portions of the lubrication circuit 108 require targeted repair, which can save time, money, and other resources.

As mentioned above, existing lube monitoring systems/ techniques generally output only overall/global lubricant health, temperature, and/or pressure. They do not provide comprehensive compositional information of the lubricant (e.g., identifying substantially full composition of the lubricant at the measurement location including chemical components that are supposed to be present, rather than merely indicating the presence of a few specific contaminants). Also, they do not determine or suggest specific portions of the lubrication circuit that are likely to require repair or inspection (e.g., specifically identifying the channels, pipes, tanks, and/or other components of the lubrication circuit that should be targeted for maintenance, rather than generically warning that some maintenance on the lube circuit is required). Overall, existing systems/technique do not provide as comprehensive and granular diagnostics as various embodiments of the subject claimed innovation.

Figure 2:
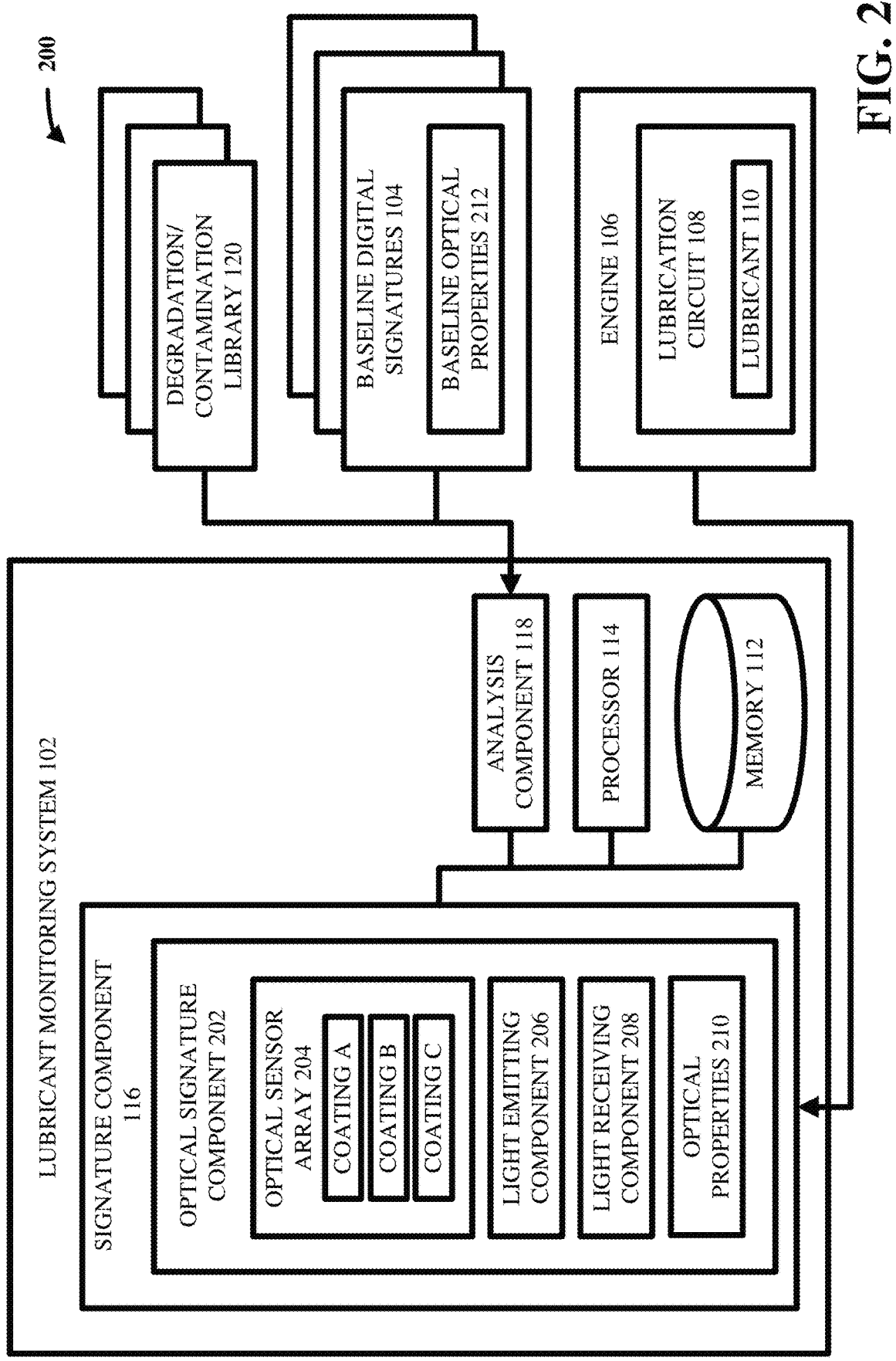
FIG. 2 illustrates a block diagram of an example, non-limiting system including an optical signature component that facilitates detection of fuel in oil, lube degradation, and foreign object contamination through optical characterization in accordance with one or more embodiments described herein.

FIG. 2 illustrates a block diagram of an example, non-limiting system 200 including an optical signature component that can facilitate detection of fuel in oil, lube degradation, and foreign object contamination through optical characterization in accordance with one or more embodiments described herein. As shown, the system 200 can, in various embodiments, comprise the same components as the system 100, and can further comprise an optical signature component 202.

As shown, in various embodiments, the optical signature component 202 can comprise an optical sensor array 204, a light emitting component 206, and a light receiving component 208. In various cases, the optical signature component 202 can leverage the optical sensor array 204, the light emitting component 206, and the light receiving component 208 in order to determine one or more optical properties 210. As mentioned above, the optical properties 210 can represent optical behavior and/or optical characteristics (e.g., UV, IR, and/or visible fluorescence intensity; UV, IR, and/or visible reflectance intensity; UV, IR, and/or visible absorbance intensity; UV, IR, and/or visible scatter intensity; UV, IR, and/or visible interference intensity; and so on) exhibited by the optical sensor array 204 when the optical sensor array 204 is coupled to the lubrication circuit 108 and exposed to the lubricant 110.

In various embodiments, the optical sensor array 204 can comprise a substrate on which there can be arranged one or more chemo-responsive optical coatings (e.g., coating A, coating B, coating C, and so on). Although for purposes of illustration FIG. 2 depicts only three chemo-responsive optical coatings in the optical sensor array 204, any suitable and/or desired number of coatings can be implemented in various embodiments. In one or more instances, a chemo-responsive optical coating can be constructed from carbon nanotubes (e.g., single-walled carbon nanotubes, multi-walled carbon nanotubes, carbon nanotube-polymer-barrier mixtures to manipulate selectivity, and so on). In one or more instances, a chemo-responsive optical coating can be constructed from graphene flakes and/or graphite oxide (e.g., structurally colored coating based on graphene and/or graphite that experiences electrical and/or visual changes in response to chemical interaction; when stressed, graphene layers can compress and flatten, thereby changing interference patterns and wavelengths of reflected light). In one or more instances, a chemo-responsive optical coating can be constructed from garnet phosphor materials having enhanced spectral characteristics. In various embodiments, a chemo-responsive optical coating can be based on any suitable chemoresistor that exhibits changes in electrical and/or optical properties in response to changes in its chemical environment (e.g., metal-oxide semiconductors, conductive polymers, nanoparticles, and so on). In various aspects, any combination of the aforementioned chemoresistors can be used to construct one or more chemo-responsive optical coatings on the optical sensor array 204.

In various instances, known techniques can be used to design a chemo-responsive optical coating to have a particular and/or desired level of selectivity (e.g., designed to interact only with a certain desired chemical, designed to interact with a few desired chemicals, designed to interact with many desired chemicals, and so on). In various instances, a chemo-responsive optical coating can exhibit high selectivity (e.g., a coating that reacts only with oxides, which can be used to detect the presence and/or concentration of oxides in the lubricant 110). In various instances, a chemo-responsive optical coating can exhibit low selectivity (e.g., interacts with oxides, silicates, nitrides, fuel, moisture, and so on, which can be used to detect the presence and/or concentration of oxides, silicates, nitrides, fuel, moisture, and so on in the lubricant 110). In various instances, a chemo-responsive optical coating can be designed to exhibit an intermediate level of selectivity as desired, and so on. In some cases, a chemo-responsive optical coating that has low selectivity can react in the same way and to the same extent with the various chemicals to which it is selective (e.g., the coating can exhibit substantially similar fluorescence intensity, reflectance intensity, absorbance intensity, scatter intensity, and interference intensity when it interacts with any chemical to which it is selective). In such embodiments, the coating cannot be used to distinguish between those chemicals (e.g., a coating that interacts identically with chemical X and chemical Y cannot be used to determine whether the detected analyte is chemical X or chemical Y). In some cases, however, a chemo-responsive optical coating that has low selectivity can nevertheless interact differently and/or to different extents with the various chemicals to which it is selective (e.g., the coating can exhibit at least one substantially different fluorescence intensity, reflectance intensity, absorbance intensity, scatter intensity, or interference intensity when it interacts with different chemicals to which it is selective). In such embodiments, the coating can be used to distinguish between those chemicals (e.g., a coating that produces a certain optical signature when it interacts with chemical X and a different optical signature when it interacts with chemical Y can be used to determine whether the detected analyte is chemical X or chemical Y). Any suitable techniques for modulating and/or manipulating chemical selectivity can, in various embodiments, be implemented.

In one or more embodiments, a chemo-responsive optical coating can react to physical interactions between it and the lubricant 110, and not just to chemical interactions between it and the lubricant 110. In one or more embodiments, a chemo-responsive optical coating can be designed to interact chemically and/or physically with any suitable and/or desired material (e.g., oxides, silicates, metallics, nitrides, sulphides, phenolics, esters, amines, aromatics, naphthenes, alkanes, asphaltics, coke, slag/sludge, varnish, moisture, fuel, dust, dirt, oil additives, and so on).

In various cases, a chemo-responsive optical coating can exhibit unique optical behavior (e.g., fluorescence intensity, reflectance intensity, absorbance intensity, scatter intensity, interference intensity, and so on) in response to chemical and/or physical interactions with the lubricant 110 depending on the chemical constituents and/or physical characteristics of the lubricant 110 (e.g., a first optical behavior/signature in the presence of heavy coking, a second optical behavior/signature in the presence of moderate slag, a third optical behavior/signature in the presence of light varnish, different optical behaviors/signatures in the presence of different combinations of the above, and so on). In various instances, this unique optical behavior can be observed and/or captured (e.g., via exemplars in the degradation/contamination library 120) and learned (e.g., used to train the analysis component 118). Thus, the signature component 116 can generate and/or measure optical properties 210, based on one or more chemo-responsive optical coatings of the sensor array 204, as a current digital signature corresponding to the lubricant 110. The analysis component 118, which can be trained to learn how the one or more chemo-responsive optical coatings of the sensor array 204 behave in response to various chemical and/or physical interactions, can determine a health and/or composition of the lubricant 110 based on comparing the optical properties 210 to baseline optical properties 212. In various embodiments, the more chemo-responsive optical coatings that are included on the optical sensor array 204 (e.g., so as to detect many different types of chemical and/or physical characteristics of the lubricant 110), the more comprehensive the health and/or compositional analysis outputted by the analysis component 118 can be.

In various embodiments, the optical sensor array 204 can include a substrate, and one or more chemo-responsive coatings (e.g., coating A, coating B, coating C, and so on) deposited on and/or otherwise suitably coupled to the substrate. In various embodiments, the substrate can be transparent (e.g., glass, plastic, and so on). In various embodiments, the optical sensor array 204 can be coupled to the lubrication circuit 108 such that it is exposed to the lubricant 110 (e.g., the substrate can be attached to the inside of an oil tank or oil sump in the lubrication circuit 108, the substrate can be attached to the inside of a channel, line, pipe, or tube of the lubrication circuit 108, and so on). The portion of the oil tank, sump, channel, line, pipe, and/or tube to which the optical sensor array 202 is coupled can, in various instances, be transparent (e.g., glass oil tube, glass sight window in oil tank, and so on).

The light emitting component 206 can be suitably positioned near the lubrication circuit 108 and can emit one or more first lights through the transparent tube/tank wall (as well as through the transparent substrate) and onto the coatings of the optical sensor array 204. In various cases, the one or more first lights can be in the UV, IR, and/or visible spectrum (e.g., UV light, IR light, blue light, and so on). In various cases, multi-laser light inputs of various wavelengths can be implemented (e.g., simultaneously emitting by the light emitting component 206 a plurality of lights of various wavelengths onto the optical sensor array 204). In various instances, the one or more first lights can be in any other suitable portion and/or range of the electromagnetic spectrum. In some embodiments, the light emitting component 206 can emit multiple first lights, beginning with a certain wavelength and progressively increasing and/or decreasing the wavelength, thereby irradiating the optical sensor array 204 with lights from a range of wavelengths. In various cases, the light emitting component 206 can be any suitable light emitting device (e.g., one or more incandescent lights, one or more light emitting diodes, one or more IR emitting sources, one or more UV emitting sources, and so on).

In response to receiving the first light, the optical sensor array 204 can emit one or more second lights (e.g., via reflection, refraction, fluorescence, radiation, and so on). These one or more second lights can be received by the light receiving component 208, which can be suitably positioned near the lubrication circuit 108. In various embodiments, the light receiving component 208 can be any suitable light receiving device (e.g., one or more IR and/or UV cameras, one or more photoresistors, and so on).

The optical signature component 202 can generate the optical properties 210 of the optical sensor array 204 based on the one or more first lights and the one or more second lights. For instance, a fluorescence intensity level, a reflectance intensity level, an absorbance intensity level, a scatter intensity level, and/or an interference intensity level of one or more chemo-responsive optical coatings of the optical sensor array 204 can be determined by comparing the characteristics of the second light to those of the first light (e.g., comparing wavelength, comparing luminosity, comparing power/intensity, and so on). In some embodiments, a level of specific coating deterioration of one or more of the chemo-responsive optical coatings can be determined based on the first light and the second light. In various cases, such specific coating deterioration can also be used to identify/characterize the health and/or composition of the lubricant 110 (e.g., different coatings of the optical sensor array 204 can deteriorate in different ways depending on the chemical and/or physical characteristics of the lubricant 110).

The signature component 116 can, in various embodiments, generate a digital signature corresponding to the optical properties 210. Since the chemo-responsive optical coatings on the optical sensor array 204 can exhibit different optical properties 210 (e.g., different optical patterns/signatures/behaviors) based on the health and/or composition of the lubricant 110, the generated digital signature can be said to correspond to the health and/or composition of the lubricant 110. In various embodiments, the optical properties 210 can be considered the digital signature.

In various aspects, the analysis component 118 can receive the optical properties 210, which can be considered the digital signature of the lubricant 110, and can compare them with baseline optical properties 212, from the baseline digital signatures 104. As mentioned above, the analysis component 118 can perform this comparison via a trained machine learning algorithm and can output as a result a comprehensive report of health and/or composition of the lubricant 110 at the location of the optical sensor array 204. In various embodiments, a plurality of optical sensor arrays 204 can be incorporated, each being placed at a different location along the flow path of the lubrication circuit 108.

To help clarify the above subject matter, consider the following illustrative and nonlimiting example. Suppose that the lubricant monitoring system 102 has a single optical sensor array 204 coupled to an internal surface of a channel in the lubrication circuit 108, the channel linking an oil sump (upstream) to an oil pump (downstream). Further, suppose that the optical sensor array 204 has seven chemo-responsive optical coatings: coatings A-C and coatings D-G (not shown in FIG. 2). Coating A can be selective to alkanes, coating B can be selective to naphthenes, coating C can be selective to aromatics, coating D can be selective to asphaltics, coating E can be selective to metallics, coating F can be selective to silicates, and coating G can be selective to fuel. In this example, the light emitting component 206 can emit one or more first lights (e.g., emitting light with a wavelength near 100 nm and progressively increasing the wavelength to over 10,000 nm in order to span a desired range of the electromagnetic spectrum, and so on) onto the optical sensor array 204. The coatings A-G can receive the one or more first lights and can emit (e.g., reflect, refract, fluoresce, scatter, radiate, and so on) one or more second lights in response. The light receiving component 208 can receive the one or more second lights. Based on the one or more first and second lights, the optical signature component 202 can determine optical properties 210 (e.g., fluorescence intensities of coatings A-G, reflectance intensities of coatings A-G, absorbance intensities of coatings A-G, scatter intensities of coatings A-G, interference intensities of coatings A-G, and so on). The analysis component 118 can then compare the optical properties 210 with the baseline optical properties 212 (fluorescence, reflectance, absorbance, scatter, interference, and so on of the coatings A-G when exposed to a healthy lubricant 110). The analysis component 118 can be trained on prior optical properties exhibited by the coatings A-G of the optical sensor array 204 when exposed to known chemicals and/or known lubricant health levels and/or compositions (e.g., trained on the degradation/contamination library 120). Thus, the analysis component 118 can infer the composition, and therefore the health, of the lubricant 110 between the oil pump and the oil sump based on the optical properties 210.

For instance, the analysis component 118 can determine that the fluorescence intensity, reflectance intensity, absorbance intensity, scatter intensity, interference intensity, and/or specific coating deterioration currently exhibited by coating A is/are similar to those that were exhibited by coating A when exposed to a lubricant known to have 22% alkanes. Similarly, the analysis component 118 can determine that the fluorescence intensity, reflectance intensity, absorbance intensity, scatter intensity, interference intensity, and/or specific coating deterioration currently exhibited by coating B is/are similar to those that were exhibited by coating B when exposed to a lubricant known to have 38% naphthenes. Likewise, the analysis component 118 can determine that the optical properties currently exhibited by coating C are similar to those that were exhibited by coating C when exposed to a lubricant known to have 27% aromatics. In the same fashion, the analysis component 118 can determine that the optical properties currently exhibited by coating D are indicative of 3% asphaltics, that the optical properties currently exhibited by coating E are indicative of 2% metallics, that the optical properties currently exhibited by coating F are indicative of 3% silicates, and that the optical properties currently exhibited by coating G are indicative of 5% fuel. Thus, the analysis component 118 can indicate and/or determine that the lubricant 110 between the sump and the pump has approximately the following composition: 22% alkanes, 38% naphthenes, 27% aromatics, 3% asphaltics, 2% metallics, 3% silicates, and 5% fuel. The analysis component 118 can determines that such a composition represents too low amounts of alkanes, naphthenes, and asphaltics, and too high amounts of aromatics, metallics, silicates, and fuel. In various embodiments, the analysis component 118 can determine whether the health of the lubricant is slightly, moderately, and/or extremely poor based on this composition (e.g., by comparing to stored compositions known to be healthy and/or to known levels of health).

Figure 3:
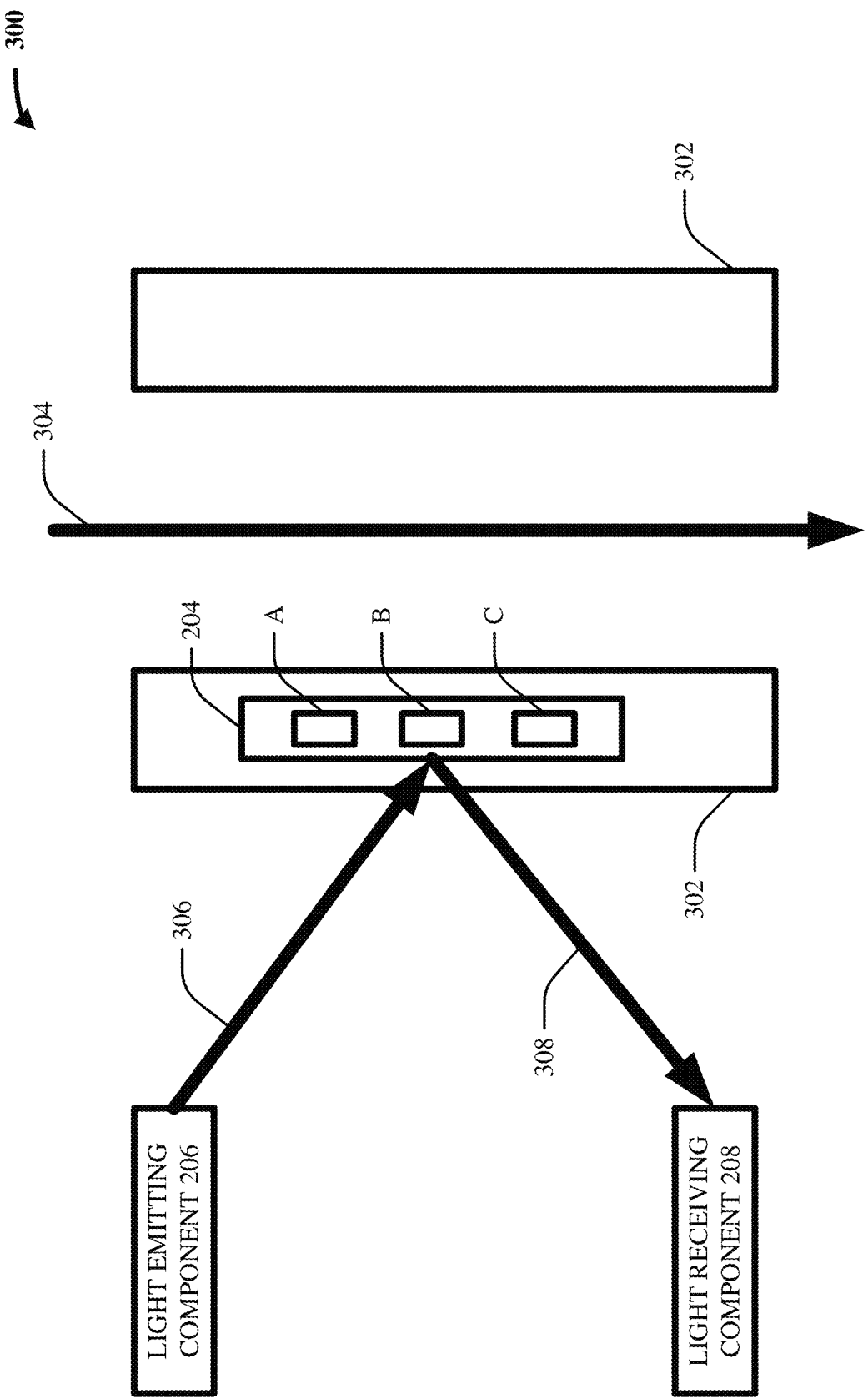
FIG. 3 illustrates a high-level schematic diagram of an example, non-limiting configuration of an optical signature component that facilitates detection of fuel in oil, lube degradation, and foreign object contamination through optical characterization in accordance with one or more embodiments described herein.

FIG. 3 illustrates a high-level schematic diagram of an example, non-limiting configuration 300 of an optical signature component that can facilitate detection of fuel in oil, lube degradation, and foreign object contamination through optical characterization in accordance with one or more embodiments described herein.

As shown, FIG. 3 depicts the optical sensor array 204, having coatings A-C, being coupled (e.g., physically attached to) an interior surface of a channel 302 (depicted as a cross-sectional profile), which can be a pipe, tube, and/or oil line in the lubrication circuit 108. The arrow 304 designates a possible flow direction of the lubricant 110 through the channel 302. As shown, the light emitting component 206 can emit one or more first lights 306 onto the optical sensor array 204. In various instances, the channel 302 can include one or more partially and/or wholly transparent wall portions (e.g., glass walls/windows in the channel 302), so that the one or more first lights 306 can pass through a transparent portion of the wall of the channel 302 and reach the optical sensor array 204. In response, the optical sensor array 204 can emit (e.g., reflect, fluoresce, refract, radiate, and so on) one or more second lights 308, which can be received by the light receiving component 208. As explained thoroughly above, the one or more first and second lights can then be used to determine optical properties 210 exhibited by the coatings A-C of the optical sensor array 204. Since the optical behavior of the coatings A-C of the optical sensor array 204 can depend on the composition and/or health of the lubricant 110, the optical properties 210 can be used to characterize the composition and/or health of the lubricant 110 via the analysis component 118.

For ease of illustration, FIG. 3 depicts the light emitting component 206 generally irradiating the optical sensor array 204 with the one or more first lights 306, and also depicts the optical sensor array 204 generally irradiating the light receiving component 208 with the one or more second lights 308. However, in various embodiments, each of the coatings A-C can independently/separately receive the one or more first lights 306, and each of the coatings A-C can independently/separately emit their own corresponding second lights (e.g., coating A can emit a light have a particular wavelength and/or other properties in response to the one or more first lights 306, coating B can emit a light having a different wavelength and/or other properties in response to the one or more first lights 306, coating C can emit a light having yet another different wavelength and/or other properties in response to the one or more first lights 306, and so on). In such embodiments, the light receiving component 208 can receive a second light from each coating of the optical sensor array 204, with the optical properties of each second light corresponding to an identity and/or concentration of a chemical and/or physical condition to which the coating that emitted the light is selective.

In various embodiments, the optical sensor array 204 can be built into the channel 302, rather than being coupled to the interior surface area of the channel 302. In any case, the coatings A-C can be physically exposed to the lubricant 110 to facilitate chemical and/or physical interaction between the coatings A-C and the lubricant 110.

It should be appreciated that FIG. 3 is illustrative only, is not drawn to scale, and is not drawn to depict actual component locations, distances, angular orientations, and so on. In various embodiments, the light emitting component 206 and the light receiving component 208 can be in any suitable location with respect to the optical sensor array 204.

FIG. 4 illustrates a high-level schematic diagram of an example, non-limiting configuration 400 of a sensor array that can facilitate detection of fuel in oil, lube degradation, and foreign object contamination through optical characterization in accordance with one or more embodiments described herein.

As shown, FIG. 4 depicts an exemplary, nonlimiting, and illustrative configuration for coupling the optical sensor array 204 to the inner surface of the channel 302. The configuration 402 depicts an example of chemo-responsive optical coatings being arranged in a ring configuration around the interior surface area of the channel 302. As shown, each of coatings A-C can wrap radially around the interior surface area of the channel 302. In various embodiments, the coatings A-C can wrap only partially radially around the interior surface area of the channel 302 (e.g., where the length of each of the coatings A-C is less than the interior circumference of the channel 302). In various embodiments, the coatings A-C can wrap fully around the interior surface area of the channel 302 (e.g., where the length of each of the coatings A-C is substantially equal to the interior circumference of the channel 302).

In various instances, it can be beneficial to use longer chemo-responsive optical coatings in a radial configuration (e.g., such that the coatings wrap fully radially around the channel 302). In such cases, the coatings can wrap more fully around the inner surface area of the channel 302, which can cause the coatings to be exposed to a greater surface area of the lubricant 110 at a single flow cross-section in the channel 302. Such a configuration can, in some instances, reduce a likelihood of obtaining false negative readings by helping to reduce the likelihood of a contaminant flowing past the coatings without sufficiently interacting with them. Generally, existing systems/techniques for monitoring engine lube assume that the lubricant is homogenous and/or uniformly mixed (e.g., this is why existing systems/techniques sense chemical and/or physical properties of lubricants using only a single sensor without regard to the positioning of the sensor along the flow path or along a cross-section perpendicular to the flow path). However, such an assumption is not necessarily true; engine lube can be non-uniform both along a flow path of the lubrication circuit and/or along a channel cross-section perpendicular to the flow path. Because real-world lubricants can be heterogeneous, false negative readings from lube monitoring systems are possible (e.g., the monitoring system can falsely indicate that there is no contaminant in the lube, because the contaminant flowing in the lube passed by the system's sensor at a sufficiently far distance to prevent the sensor from being triggered).

In various cases, the radial coupling of configuration 402 can eliminate and/or help to reduce such false negatives. For instance, consider coating A. As shown, coating A can, in some cases, wrap fully radially around the inner surface area of the channel 302, thereby circumscribing its own corresponding control volume within the channel 302 (e.g., defined by the circumference and width of coating A). Any contaminant that is flowing through the lubricant 110 must pass through some portion of this control volume; otherwise, the contaminant is stationary (e.g., coke). Moreover, no point within this control volume is more than a radial distance away from a portion of coating A. If coating A were instead wrapped only partially radially around the inner surface area of the channel 302, there would exist a path through the circumscribed control volume the closest distance to coating A of which would be greater than a radius of the channel 302. In various cases, the greater the distance is between a contaminant and a chemical sensor, the more likely it is that the contaminant can "sneak" past the sensor (e.g., pass by without triggering the sensor). As an example, if coating A were wrapped only around a small portion of the inner surface area of channel 302 (e.g., a small portion of the circumference of channel 302), then it would be possible for contaminants to which coating A is selective to flow past coating A but nearer the unwrapped portions of the inner surface area of the channel 302 (e.g., if coating A is on the left side of a cross-section of the channel 302, contaminants can potentially "sneak" past if they flow far enough to the right side of the cross-section). This can also apply to stationary contaminants, like coking (e.g., if coating A is on an upper side of a cross-section of the channel 302, a likelihood of failing to identify coking formed on the bottom side of the cross-section but not on the upper side of the cross-section can be increased). Such a configuration can increase the likelihood of a false negative reading. By minimizing the distance between coating A and every point in coating A's circumscribed control volume, the configuration 402 can help to reduce the possibility that a flowing contaminant and/or stationary contaminant remains undetected by coating A.

Since coatings B and C also wrap fully radially around the inner surface area of the channel 302, they also circumscribe their own corresponding control volumes within the channel 302 and thus can achieve the same benefit (e.g., reduced false negatives). In various aspects, the configuration 402 can be referred to as a ring array of coatings, with each chemo-responsive optical coating wrapping radially around an inner surface area of the channel 302.

Nevertheless, various embodiments of the subject claimed innovation can include coatings that do not wrap fully radially around the inner surface of the channel 302. In various embodiments, other configurations of the coatings are possible. Configuration 404 shows one such example, where the coatings A-C are arranged in parallel around the inner surface area of the channel 302 and extend longitudinally along the channel 302. The configuration 404 can, in various aspects, be referred to as a parallel array of coatings, with each chemo-responsive optical coating extending longitudinally along the channel 302.

It should be noted that FIG. 4 is not drawn to scale, is illustrative, and is exemplary and nonlimiting only.

Figure 5:
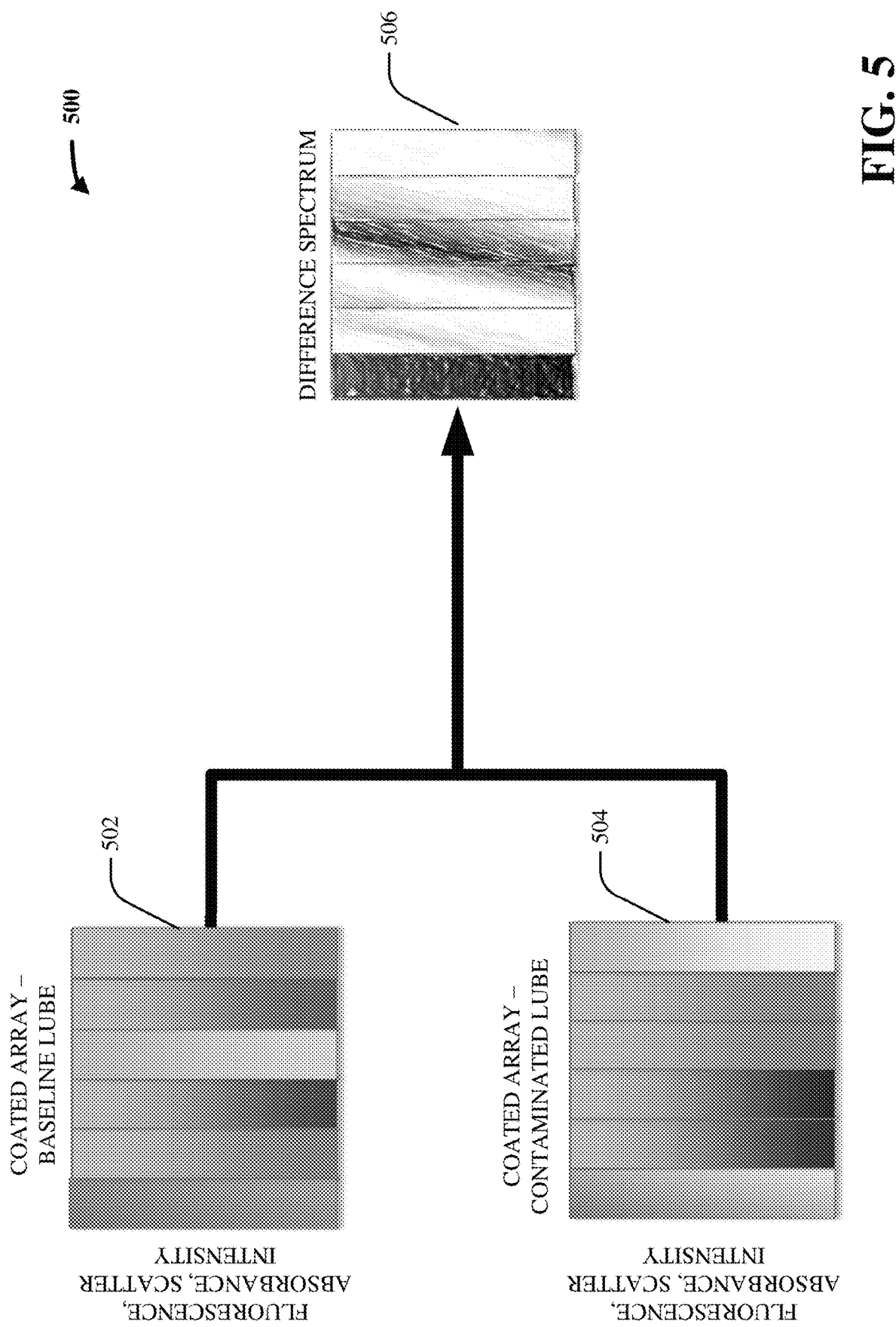
FIG. 5 illustrates a high-level diagram of example, non-limiting changes in optical properties of a sensor array that facilitates detection of fuel in oil, lube degradation, and foreign object contamination through optical characterization in accordance with one or more embodiments described herein.

FIG. 5 illustrates a high-level diagram 500 of example, non-limiting changes in optical properties of a sensor array that facilitates detection of fuel in oil, lube degradation, and foreign object contamination through optical characterization in accordance with one or more embodiments described herein.

As shown, FIG. 5 depicts coated array 502 corresponding to baseline lube. That is, coated array 502 represents illustrative optical properties (e.g., UV, IR, and/or visible fluorescence intensity, reflectance intensity, absorbance intensity, scatter intensity, interference intensity, and/or so on) exhibited by each coating of an optical sensor array (e.g., optical sensor array 204) that has six chemo-responsive optical coatings (e.g., six colored columns in the figure) and that has been exposed to a healthy and/or acceptably contaminated lubricant. Similarly, coated array 504 can correspond to contaminated lube. That is, coated array 504 can represent illustrative optical properties exhibited by each coating of an optical sensor array having six chemo-responsive optical coatings and that has been exposed to an unacceptably contaminated lubricant. As explained thoroughly above, each coating of the array can receive one or more first lights and emit their own corresponding one or more second lights with their own corresponding optical characteristics (e.g., wavelength, power/intensity, luminescence, and so on). The optical response of each coating can then be used to characterize the health and/or composition of the lubricant 110. Specifically, a difference spectrum 506 can be generated by comparing the optical behavior/response of the coated array 502 (baseline) to the optical behavior/response of the coated array 504 (contaminated) (e.g., comparing the optical properties exhibited by each coating when exposed to healthy lube with the optical properties exhibited by each coating when exposed to contaminated lube). This difference spectrum can then be analyzed by the analysis component 118 to characterize the health and/or composition of the lubricant 110.

It should be noted that FIG. 5 is exemplary, illustrative, and nonlimiting only.

Figure 6:
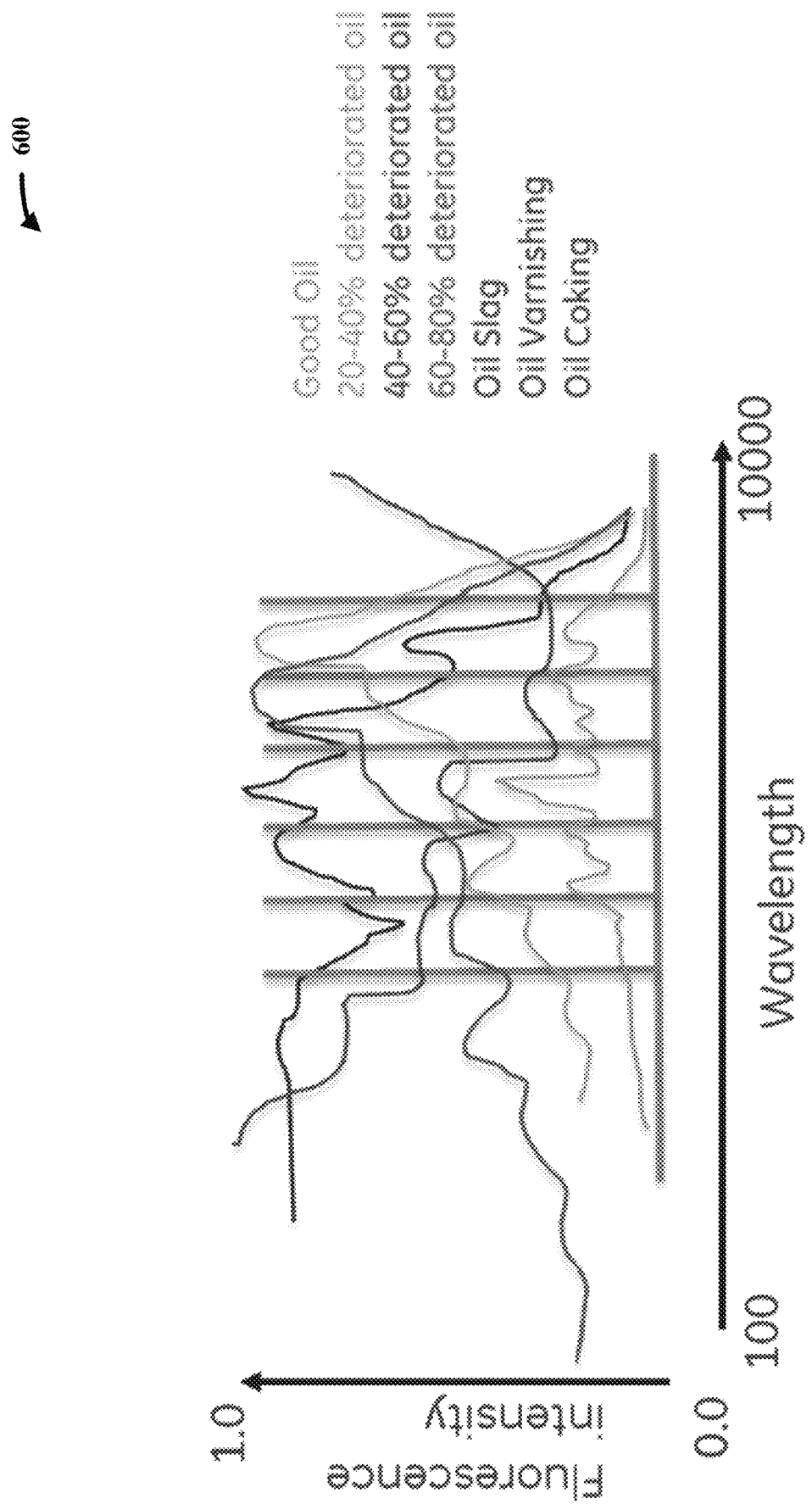
FIG. 6 illustrates an example, non-limiting graph of changes in optical properties of a sensor array that facilitates detection of fuel in oil, lube degradation, and foreign object contamination through optical characterization in accordance with one or more embodiments described herein.

FIG. 6 illustrates an example, non-limiting graph 600 of changes in optical properties of a sensor array that can facilitate detection of fuel in oil, lube degradation, and foreign object contamination through optical characterization in accordance with one or more embodiments described herein.

As shown, the graph 600 depicts fluorescence intensity exhibited by a chemo-responsive coating of an optical sensor array (e.g., coating A of optical sensor array 204) as a function of wavelength (e.g., as a function of the wavelength of the one or more first lights 306 that are emitted onto the optical sensor array 204). As shown, the fluorescence intensity exhibited by the optical sensor array can vary both with wavelength and with health and/or composition of the lubricant (e.g., lubricant 110). Thus, for a given lubricant, the one or more first lights 306 emitted by the light emitting component 206 can be used to determine how one or more optical properties and/or optical behaviors (e.g., fluorescence intensity, and so on) of a coating of the optical sensor array 204 vary across the electromagnetic spectrum (e.g., by varying the wavelength of the one or more first lights 306 from as little as 100 nm to as high as 10,000 nm, varying across any other desired wavelength range, and so on). Once the optical behavior/signature of the coating of the optical sensor array 204 is determined (e.g., by measuring fluorescence intensity of the coating A of the sensor array 204 in response to the one or more first lights 306 across the electromagnetic spectrum), it can be analyzed by the analysis component 118. As mentioned above, the analysis component 118 can be trained on optical signatures exhibited by the optical sensor array 204 when exposed to known lubricant healths and/or compositions (e.g., trained on fluorescence signatures like those depicted in graph 500). Thus, the optical behavior of the optical sensor array 204 can be used to characterize health and/or composition of the lubricant 110. In various cases, each coating on an optical sensor array can have its own corresponding optical behavior/response (e.g., the fluorescence intensity behavior of coating A of the optical sensor array 204 can correspond to and/or be shown by the graph 600, the fluorescence intensity behavior of coating B of the optical sensor array 204 can correspond to and/or be shown by a different graph, the fluorescence intensity behavior of coating C of the optical sensor array 204 can correspond to and/or be shown by a still different graph, and so on).

It should be noted that FIG. 6 is exemplary, illustrative, and nonlimiting only. Furthermore, it should be understood that similar graphs can be constructed for any other suitable optical property of a chemo-responsive optical coating (e.g., reflectance intensity, absorbance intensity, scatter intensity, interference intensity, specific coating deterioration, and so on).

In various embodiments, more than one optical property of each coating of the optical sensor array 204 can be measured in order to reduce a likelihood of false negative readings.

Figure 7:
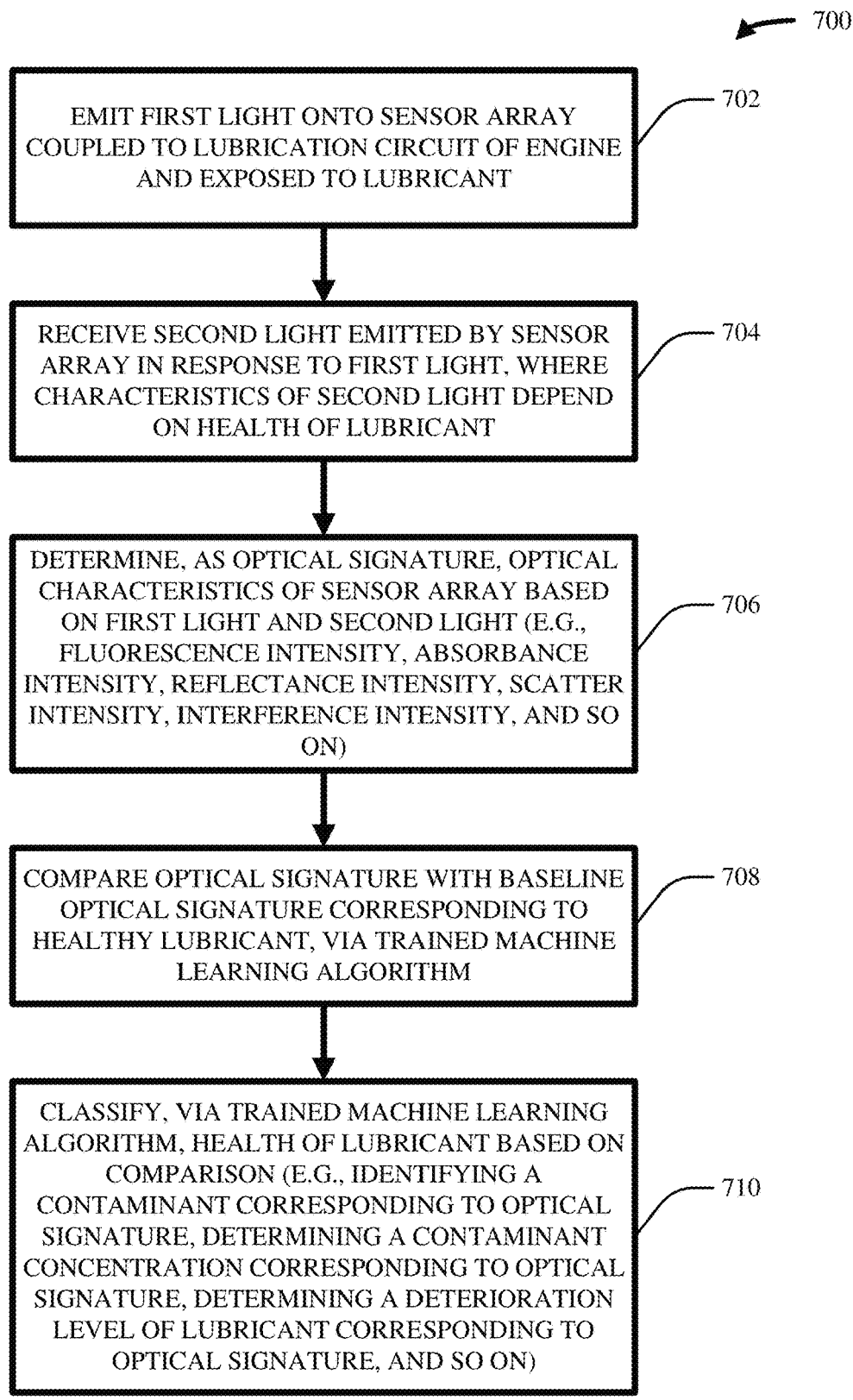
FIG. 7 illustrates a high-level flow diagram of an example, non-limiting computer-implemented method that facilitates detection of fuel in oil, lube degradation, and foreign object contamination through optical characterization in accordance with one or more embodiments described herein.

FIG. 7 illustrates a high-level flow diagram of an example, non-limiting computer-implemented method 700 that facilitates detection of fuel in oil, lube degradation, and foreign object contamination through optical characterization in accordance with one or more embodiments described herein.

In various embodiments, act 702 can include emitting a first light (e.g., first light 306) onto a sensor array (e.g., optical sensor array 204) that is coupled to a lubrication circuit (e.g., lubrication circuit 108) of an engine (e.g., engine 106) and that is exposed to a lubricant (e.g., lubricant 110).

In various instances, act 704 can include receiving a second light (e.g., second light 308) emitted by the sensor array in response to the first light, where characteristics of the second light (e.g., wavelength, power/intensity, and so on) depend on the health and/or composition of the lubricant.

In various aspects, act 706 can include determining, as an optical signature of the lubricant, optical characteristics (e.g., optical properties 210, such as fluorescence, reflectance, absorbance, scatter, interference, and so on) of the sensor array based on the first and second lights.

In various cases, act 708 can include comparing the optical signature with a baseline optical signature (e.g., baseline optical signatures 104) corresponding to a healthy lubricant, where the comparison is performed via a trained machined learning algorithm (e.g., analysis component 118).

In various embodiments, act 710 can include classifying, via the trained machine learning algorithm, the health and/or composition of the lubricant based on the comparison (e.g., determining identities and/or concentrations of contaminants in the lubricant, determining a deterioration level of the lubricant, and so on).

Figure 8:
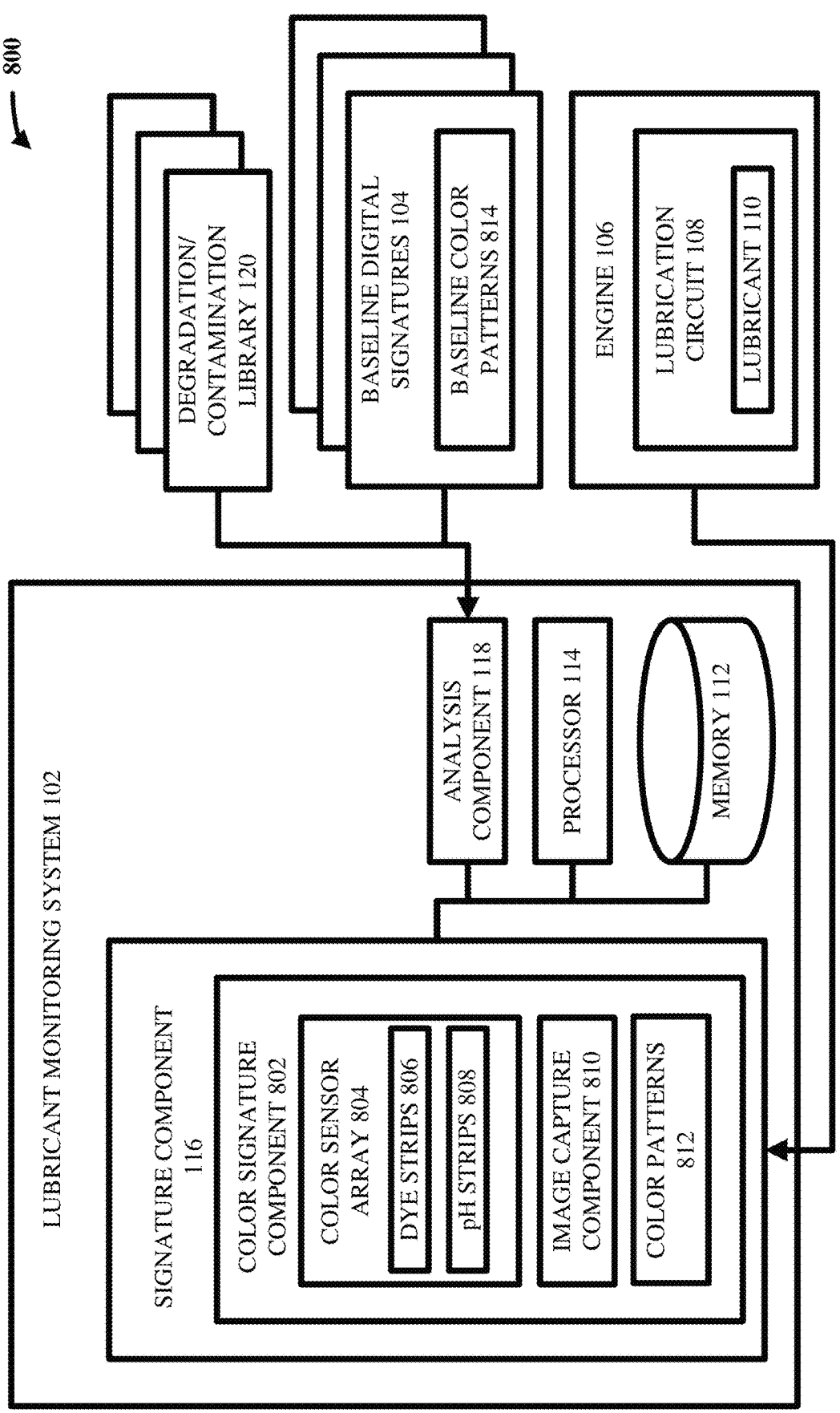
FIG. 8 illustrates a block diagram of an example, non-limiting system including a color signature component that facilitates detection of fuel in oil, lube degradation, and foreign object contamination through color characterization in accordance with one or more embodiments described herein.

FIG. 8 illustrates a block diagram of an example, non-limiting system 800 including a color signature component that can facilitate detection of fuel in oil, lube degradation, and foreign object contamination through color characterization in accordance with one or more embodiments described herein. As shown, the system 800 can, in various embodiments, comprise the same components as the system 100, and can further comprise a color signature component 802.

As shown, in various embodiments, the color signature component 802 can comprise a color sensor array 804 and an image capture component 810. In various cases, the color signature component 802 can leverage the color sensor array 804 and the image capture component 810 in order to determine one or more color patterns 812. As mentioned above, the color patterns 812 can represent arrangements/patterns of visible colors exhibited by chemo-responsive color dyes (e.g., dye strips 806) and/or pH indicator dyes (e.g., pH strips 808) exhibited by the color sensor array 804 when the color sensor array 804 is coupled to the lubrication circuit 108 and exposed to the lubricant 110.

In various embodiments, the color sensor array 804 can comprise a substrate on which there can be arranged one or more dye strips 806 (e.g., a dye strip can have one or more chemo-responsive color dyes which can change color depending on the identities of contaminants in the chemical environment) and/or one or more pH strips 808 (e.g., a pH strip can have one or more gradient-based chemo-responsive color dyes and/or colorimetric sensors which can change visible color and/or shade of visible color depending on the concentrations of contaminants in the chemical environment). In various embodiments, any suitable and/or desired number of dye strips 806 and/or pH strips 808 can be implemented.

In one or more instances, a chemo-responsive color dye on a dye strip 806 can be constructed based on any suitable color-changing chemical that can change visible color in response to chemical interaction with one or more desired chemicals (e.g., litmus tests, garnet phosphor materials with enhanced spectral characteristics, carbon nanotubes, graphene flakes, graphite oxide, and so on). In various embodiments, known techniques can be used to design a chemo-responsive color dye to have a particular and/or desired level of selectivity (e.g., designed to interact only with a certain desired chemical, designed to interact with a few desired chemicals, designed to interact with many desired chemicals, and so on). In various instances, a chemo-responsive color dye can exhibit high selectivity (e.g., a dye that changes color only when interacting with alkanes, which can be used to detect the presence of alkanes in the lubricant 110). In various instances a chemo-responsive color dye can exhibit low selectivity (e.g., a dye that changes color in the presence of oxides, amines, fuel, slag, and so on in the lubricant 110). In various instances, a chemo-responsive color dye can be designed to exhibit an intermediate level of selectivity as desired, and so on. In various embodiments, any suitable techniques for modulating and/or manipulating chemical selectivity can be implemented.

In one or more embodiments, a chemo-responsive color dye can react to physical interactions between it and the lubricant 110, and not just to chemical interactions between it and the lubricant 110 (e.g., change color when temperature and/or pressure exceed and/or fall below suitable thresholds, change color in presence of stress, and so on). In one or more embodiments, a chemo-responsive color dye can be designed to interact chemically and/or physically with any suitable and/or desired material (e.g., oxides, silicates, metallics, nitrides, sulphides, phenolics, esters, amines, aromatics, naphthenes, alkanes, asphaltics, coke, slag/sludge, varnish, moisture, fuel, dust, dirt, oil additives, and so on).

In one or more instances, a gradient-based chemo-responsive color dye and/or colorimetric sensor on a pH strip 808 can be constructed based on any suitable color-changing chemical that can gradually and/or progressively change shade of visible color in response to chemical interaction with one or more desired chemicals (e.g., litmus tests, garnet phosphor materials with enhanced spectral characteristics, carbon nanotubes, graphene flakes, graphite oxide, and so on). In various embodiments, known techniques can be used to design a gradient-based chemo-responsive color dye and/or colorimetric sensor to have a particular and/or desired level of selectivity (e.g., designed to interact only with a certain desired chemical, designed to interact with a few desired chemicals, designed to interact with many desired chemicals, and so on). In various instances, a gradient-based chemo-responsive color dye and/or colorimetric sensor can exhibit high selectivity (e.g., a dye that changes shade only when interacting with alkanes, where the level of shade change can be used to detect the concentration of alkanes in the lubricant 110). In various instances a gradient-based chemo-responsive color dye and/or colorimeter can exhibit low selectivity (e.g., a dye that changes shade in the presence of oxides, amines, fuel, slag, and so on in the lubricant 110). In various instances, a gradient-based chemo-responsive color dye and/or colorimeter can be designed to exhibit an intermediate level of selectivity as desired, and so on. In various embodiments, any suitable techniques for modulating and/or manipulating chemical selectivity can be implemented.

In one or more embodiments, a gradient-based chemo-responsive color dye and/or colorimeter can react to physical interactions between it and the lubricant 110, and not just to chemical interactions between it and the lubricant 110 (e.g., shade change when temperature and/or pressure exceed and/or fall below suitable thresholds, and so on). In one or more embodiments, a gradient-based chemo-responsive color dye and/or colorimeter can be designed to interact chemically and/or physically with any suitable and/or desired material (e.g., oxides, silicates, metallics, nitrides, sulphides, phenolics, esters, amines, aromatics, naphthenes, alkanes, asphaltics, coke, slag/sludge, varnish, moisture, fuel, dust, dirt, oil additives, and so on).

In various embodiments, a color sensor array 804 can have one or more dye strips 806 and/or one or more pH strips 808. In various embodiments, a color sensor array 804 can have one or more dye strips 806 without having one or more pH strips 808. In various embodiments, a color sensor array 804 can have one or more pH strips 808 without having one or more dye strips 806.

In various embodiments, the one or more dye strips 806 can exhibit a first color pattern and/or color signature which can identify contaminants in the lubricant 110 (e.g., a dye strip 806 having five different chemo-responsive color dyes, each selective to one of five different chemicals, can be used to determine whether each of those five chemicals are present in the lubricant 110). In various embodiments, the one or more pH strips 808 can exhibit a second color pattern and/or color signature which can identify concentration levels of contaminants in the lubricant 110 (e.g., a pH strip 808 having six different gradient-based chemo-responsive color dyes and/or colorimetric sensors, each selective to one of six different chemicals, can be used to determine concentrations levels of each of those six chemicals in the lubricant 110).

In various cases, the color sensor array 804 can exhibit unique color patterns 812 (e.g., including one or more first color patterns exhibited by the one or more dye strips 806 and one or more second color patterns exhibited by the one or more pH strips 808) in response to chemical and/or physical interactions with the lubricant 110 depending on the chemical constituents and/or physical characteristics of the lubricant 110 (e.g., first color patterns/signatures in the presence of heavy coking, second color patterns/signatures in the presence of moderate slag, third color patterns/signatures in the presence of light varnish, different color patterns/signatures in the presence of different combinations of the above, and so on). In various instances, this unique color behavior can be observed and/or captured (e.g., via exemplars in the degradation/contamination library 120) and learned (e.g., used to train the analysis component 118). 8

Thus, the signature component 116 can generate color patterns 812, based on one or more dye strips 806 and/or pH strips 808 of the color sensor array 804, as a current digital signature corresponding to the lubricant 110. The analysis component 118, which can be trained to learn how the one or more dye strips 806 and the one or more pH strips 808 of the color sensor array 804 behave in response to various chemical and/or physical interactions, can determine a health and/or composition of the lubricant 110 based on comparing the color patterns 812 to baseline color patterns 814. In various embodiments, the more chemo-responsive color dyes that are included in the one or more dye strips 806 and the more gradient-based chemo-responsive color dyes and/or colorimeter sensors that are included in the pH strips 808 of the color sensor array 804, the more comprehensive the health and/or compositional analysis outputted by the analysis component 118 can be.

In various embodiments, similar to the system 200 as explained above, the color sensor array 804 can include a substrate and the one or more dye strips 806 and the one or more pH strips 808 can be deposited on and/or otherwise suitably coupled to the substrate. In various embodiments, the substrate can be transparent (e.g., glass, plastic, and so on). In various instances, the color sensor array 804 can be coupled to an inner surface of the lubrication circuit 108 such that it is exposed to the lubricant 110 (e.g., the substrate can be attached to the inside of an oil tank or oil sump in the lubrication circuit 108, the substrate can be attached to the inside of a channel, line, pipe, or tube of the lubrication circuit 108, and so on). The portion of the oil tank, sump, channel, line, pipe, and/or tube to which the color sensor array 804 is coupled can, in various aspects, be transparent (e.g., glass oil tube, glass sight window in oil tank, and so on).

The image capture component 810 can be suitably positioned near the lubrication circuit 108 and can capture an image through the transparent tube/tank wall (as well as through the transparent substrate) of the color sensor array 804. In various cases, the image can include a first color pattern of the color sensor array 804 corresponding to an identify of a contaminant in the lubricant 110 (e.g., a first color pattern exhibited by a dye strip 806), and can include a second color pattern of the color sensor array 804 corresponding to a concentration of the contaminant in the lubricant 110 (e.g., a second color pattern exhibited by a pH strip 808).

Based on the captured image, the color signature component 802 can generate the color patterns 812 (e.g., detect the color patterns 812 of the color sensor array 804 in the image). The signature component 116 can, in various embodiments, generate a digital signature corresponding to the color patterns 812. Since the dye strips 806 and pH strips 808 on the color sensor array 804 can exhibit different color patterns 812 (e.g., different color matrices/signatures/arrangements/behaviors) based on the health and/or composition of the lubricant 110, the generated digital signature can be said to correspond to the health and/or composition of the lubricant 110. In various embodiments, the color patterns 812 can be considered the digital signature.

In various instances, the analysis component 118 can then receive the color patterns 812, which can be considered the digital signature of the lubricant 110, and can compare them with baseline color patterns 814, from the baseline digital signatures 104. As mentioned above, the analysis component 118 can perform this comparison via a trained machine learning algorithm and can output as a result a comprehensive report of the health and/or composition of the lubricant 110 at the location of the color sensor array 804. In various embodiments, a plurality of color sensor arrays 804 can be incorporated, each being placed at a different location along the flow path of the lubrication circuit 108.

In various embodiments, the color signature component 802 can be considered to function similarly (at a high level of generality) to the optical signature component 202. In various cases, they can each generate a digital signature that can be used to characterize the health and/or composition of the lubricant 110, with the primary difference being how they generate the digital signature (e.g., the optical signature component 202 can detect optical behavior in the UV, IR, and/or visible spectrum of chemo-responsive optical coatings, while the color signature component 802 can detect color patterns in the visible spectrum of color-changing dyes). In any case, the digital signature generated by the signature component 116 can be used, in various embodiments, to comprehensively characterize the composition and/or health of the lubricant 110.

Figure 9:
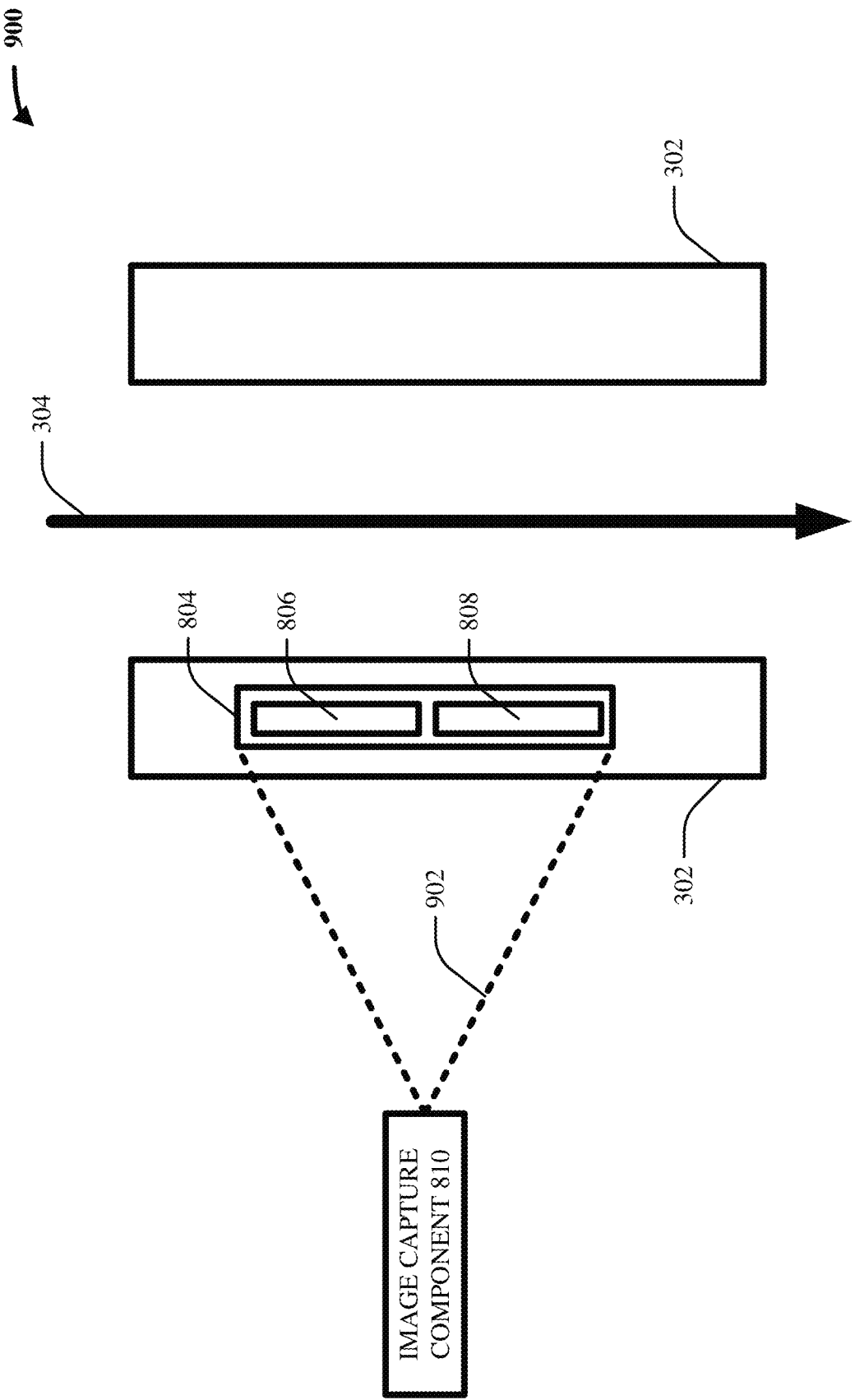
FIG. 9 illustrates a high-level schematic diagram of an example, non-limiting configuration of a color signature component that facilitates detection of fuel in oil, lube degradation, and foreign object contamination through color characterization in accordance with one or more embodiments described herein.

FIG. 9 illustrates a high-level schematic diagram of an example, non-limiting configuration 900 of a color signature component that can facilitate detection of fuel in oil, lube degradation, and foreign object contamination through color characterization in accordance with one or more embodiments described herein.

As shown, FIG. 9 depicts the color sensor array 804, having dye strips 806 and pH strips 808, being coupled (e.g., physically attached to) an interior surface of the channel 302 (depicted as a cross-sectional profile) of the lubrication circuit 108. Again, the arrow 304 designates a possible flow direction of the lubricant 110 through the channel 302. As shown, the image capture component 810 can have a field of view 902 of the color sensor array 804, thereby enabling it to capture an image of the color sensor array 804. In various instances, the channel 302 can include one or more partially and/or wholly transparent wall portions (e.g., glass walls/windows in the channel 302), so that the color sensor array 804 is in the field of view 902 of the image capture component 810. The color signature component 802 can analyze the captured image to determine color patterns 812 of the color sensor array 804 (e.g., a first color pattern of the dye strip 806 indicating identities of contaminants in the lubricant 110, and a second color pattern of the pH strip 808 indicating concentrations of contaminants in the lubricant 110). As explained thoroughly above, since the color behaviors of the dye strip 806 and the pH strip 808 can depend on the composition and/or health of the lubricant 110, the color patterns 812 can be used to comprehensively characterize the composition and/or health of the lubricant 110 via the analysis component 118.

In various embodiments, the color sensor array 804 can be built into the channel 302, rather than being coupled to the interior surface area of the channel 302. In any case, the dye strip 806 and the pH strip 808 can be physically exposed to the lubricant 110 to facilitate chemical and/or physical interaction between them and the lubricant 110.

It should be appreciated that FIG. 9 is illustrative only, is not drawn to scale, and is not drawn to depict actual component locations, distances, angular orientations, and so on. In various embodiments, the image capture component 810 can be in any suitable location with respect to the color sensor array 804.

In various embodiments, the color sensor array 804 can be configured to couple to the channel 302 radially and/or in parallel, similar to the optical sensor array 204 as described above in connection with FIG. 4.

Figure 10:
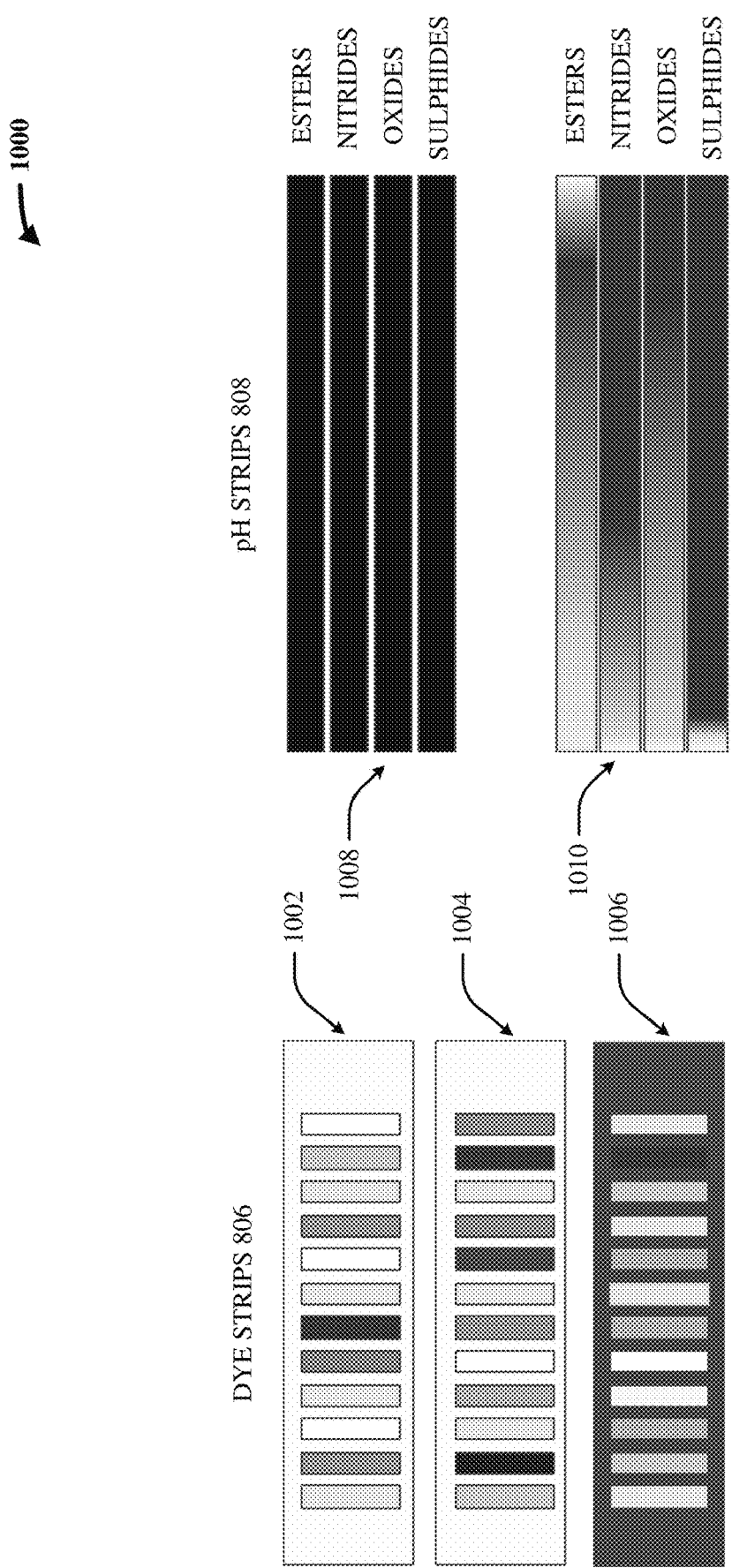
FIG. 10 illustrates a high-level diagram of example, non-limiting changes in color patterns of a sensor array that facilitates detection of fuel in oil, lube degradation, and foreign object contamination through color characterization in accordance with one or more embodiments described herein.

FIG. 10 illustrates a high-level diagram 1000 of example, non-limiting changes in color patterns of a sensor array that can facilitate detection of fuel in oil, lube degradation, and foreign object contamination through color characterization in accordance with one or more embodiments described herein.

As shown, FIG. 10 depicts dye strip 1002 corresponding to baseline lube. That is, dye strip 1002 represents illustrative color patterns (e.g., colors exhibited by a plurality of chemo-responsive color dyes) of a color sensor array (e.g., color sensor array 804), having twelve chemo-responsive color dyes (e.g., twelve colored columns in the figure) and that has been exposed to a healthy and/or acceptably contaminated lubricant. Similarly, dye strip 1004 can correspond to contaminated lube. That is, dye strip 1004 can represent illustrative color patterns of a color sensor array having twelve chemo-responsive color dyes and that has been exposed to an unacceptably contaminated lubricant. As explained thoroughly above, each color dye of the dye strip can change color based on chemical and/or physical interactions with the lubricant. The color response (e.g., the displayed color pattern of the dye strip) can then be used to characterize the health and/or composition of the lubricant. Specifically, a difference spectrum 1006 can be generated by comparing the color pattern/response of the dye strip 1002 (baseline) to the color pattern/response of the dye strip 1004

(contaminated). This difference spectrum can then be analyzed by the analysis component 118 to characterize the health and/or composition of the lubricant 110.

Similarly, FIG. 10 depicts pH strip 1008 corresponding to baseline lube. That is, pH strip 1008 represents illustrative color patterns (e.g., color gradients exhibited by a plurality of gradient-based chemo-responsive color dyes and/or colorimeter sensors) of a color sensor array, having four gradient-based chemo-responsive color dyes and/or colorimetric sensors (e.g., four colored rows in the figure) and that has been exposed to a healthy and/or acceptably contaminated lubricant. Similarly, pH strip 1010 can correspond to contaminated lube. That is, pH strip 1010 can represent illustrative color patterns of a color sensor array having four gradient-based chemo-responsive color dyes and/or colorimetric sensors and that has been exposed to an unacceptably contaminated lubricant. As explained thoroughly above, each dye of the pH strip can change shade based on chemical and/or physical interactions with the lubricant. The color response (e.g., the displayed color patterns/gradients of the pH strip) can then be used to characterize the health and/or composition of the lubricant (e.g., via comparison with baseline color patterns by the analysis component 118).

It should be noted that FIG. 10 is exemplary, illustrative, and nonlimiting only.

Figure 11:
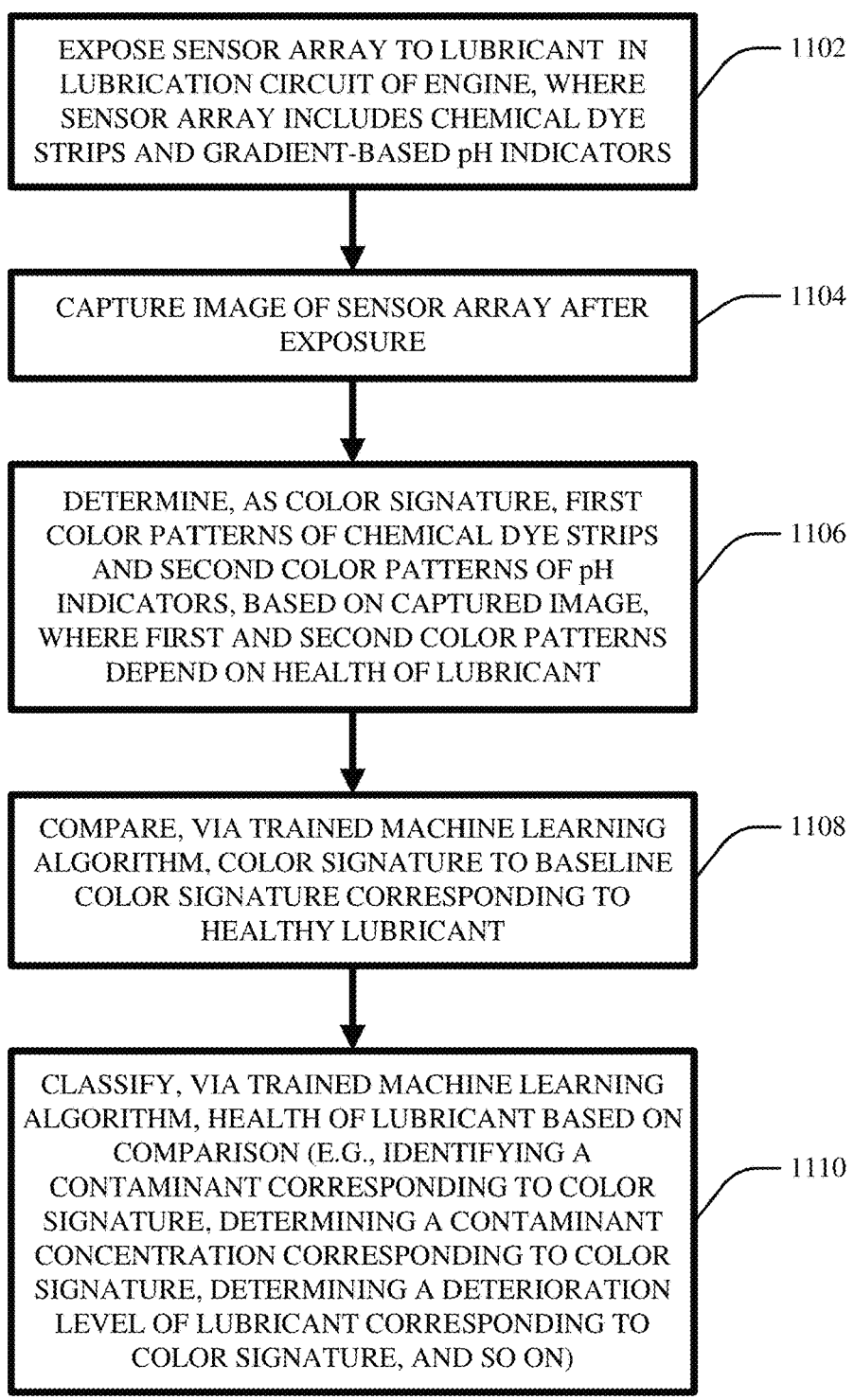
FIG. 11 illustrates a high-level flow diagram of an example, non-limiting computer-implemented method that facilitates detection of fuel in oil, lube degradation, and foreign object contamination through color characterization in accordance with one or more embodiments described herein.

FIG. 11 illustrates a high-level flow diagram of an example, non-limiting computer-implemented method 1100 that can facilitate detection of fuel in oil, lube degradation, and foreign object contamination through color characterization in accordance with one or more embodiments described herein.

In various embodiments, act 1102 can include exposing a sensor array (e.g., color sensor array 804) to a lubricant (e.g., lubricant 110) in a lubrication circuit (e.g., lubrication circuit 108) of an engine (e.g., engine 106), where the sensor array includes chemical dye strips (e.g., dye strips 806) and gradient-based pH indicators (e.g., pH strips 808).

In various instances, act 1104 can include capturing an image of the sensor array (e.g., via the image capture component 810) after exposure to the lubricant.

In various aspects, act 1106 can include determining, as a color signature, one or more first color patterns of the chemical dye strips (e.g., color patterns exhibited by the dye strips 806) and one or more second color patterns of the pH indicators (e.g., color patterns exhibited by the pH strips 808), based on the captured image, where the first and second color patterns can depend on the health and/or composition of the lubricant.

In various cases, act 1108 can include comparing, via a trained machine learning algorithm, the color signature to a baseline color signature corresponding to a healthy lubricant.

In various embodiments, act 1110 can include classifying, via the trained machine learning algorithm, the health and/or composition of the lubricant based on the comparison.

Figure 12:
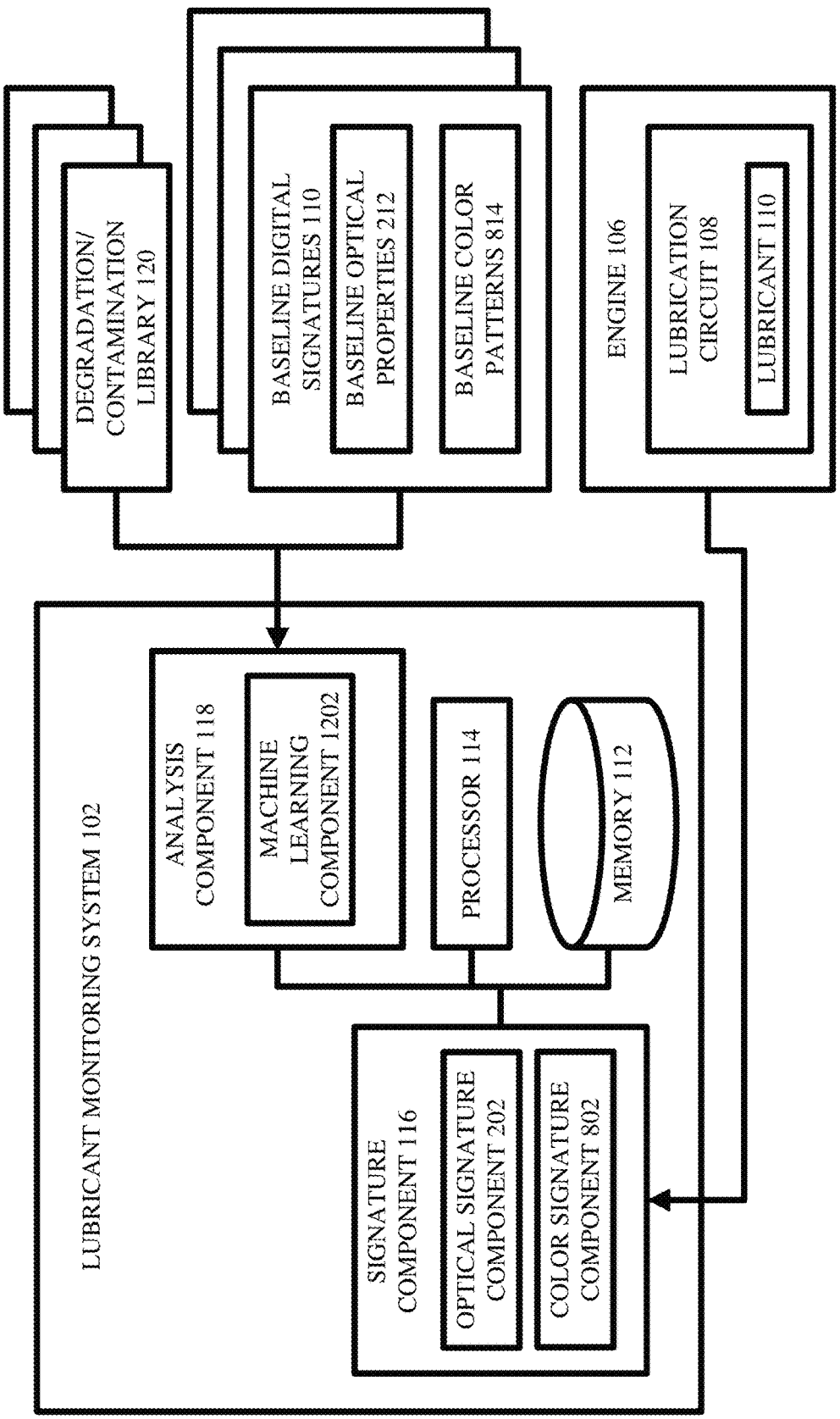
FIG. 12 illustrates a block diagram of an example, non-limiting system including a machine learning component that facilitates detection of fuel in oil, lube degradation, and foreign object contamination through optical and/or color characterization in accordance with one or more embodiments described herein.

FIG. 12 illustrates a block diagram of an example, non-limiting system 1200 including a machine learning component that can facilitate detection of fuel in oil, lube degradation, and foreign object contamination through optical and/or color characterization in accordance with one or more embodiments described herein. As shown, the system 1200 can include one and/or both of the optical signature component 202 and the color signature component 802, and can, in various embodiments, further comprise a machine learning component 1202.

As explained above, the analysis component 118 can comprehensively characterize the health and/or composition of the lubricant 110 by employing the machine learning component 1202. In various instances, the machine learning component 1202 can comprise any suitable mathematical, statistical, and/or computational classification technique. For instance, in various embodiments, the machine learning component 1202 can include any suitable mathematical, statistical, and/or computational technique that can be trained (e.g., via supervised learning on known data sets) to classify an input data set into one or more output classifications (e.g., to detect patterns and/or signatures in an input data set and to correlate the detected patterns and/or signatures to one or more states of the input data set). For example, the machine learning component 1202 can be trained (e.g., on degradation/contamination library 120 via supervised learning, unsupervised learning, reinforcement learning, and so on) to correlate a particular input data set characterizing the lubricant 110 (e.g., optical properties 210 exhibited by an optical sensor array 204 and/or color patterns 812 exhibited by a color sensor array 804) with a particular chemical composition and/or health level of the lubricant 110. In various embodiments, the machine learning component 1202 can comprise one or more linear classifiers (e.g., generative classifiers such as Naïve Bayes, linear discriminant analysis, and so on; discriminative classifiers such as logistic regression, perceptron, support vector machines, and so on; linear affine transformations optimized to achieve global minima; and so on). In various embodiments, the machine learning component 1202 can comprise one or more non-linear classifiers (e.g., artificial neural networks, non-linear and/or high dimensional support vector machines, and so on).

In one or more embodiments, the machine learning component 1202 can be trained on the degradation/contamination library 120 in order to learn correlations between the digital signatures generated by the optical signature component 202 and the composition and/or health of the lubricant 110, and/or to learn correlations between the digital signatures generated by the color signature component 802 and the composition and/or health of the lubricant 110.

To facilitate the above-described machine learning aspects of various embodiments of the subject claimed innovation, consider the following discussion of artificial intelligence. Various embodiments of the present innovation herein can employ artificial intelligence (AI) to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute, and so on) of the present innovation, components of the present innovation can examine the entirety or a subset of the data to which it is granted access and can provide for reasoning about or determine states of the system, environment, and so on from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z1, z2, z3, z4, zn)$, to a confidence that the input belongs to a class, as by $f(z)$=confidence(class). Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Figure 13:
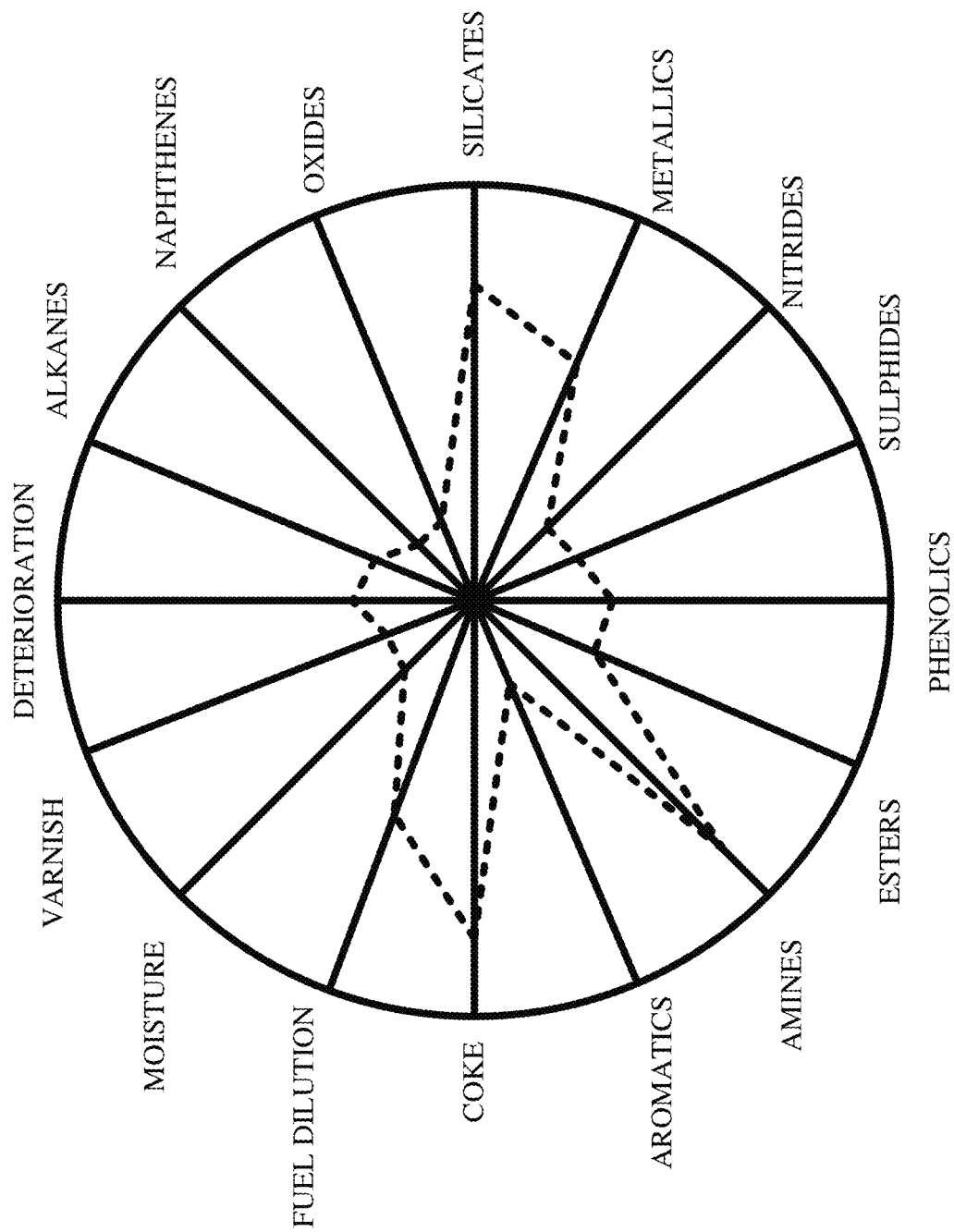
FIG. 13 illustrates an example, non-limiting graph of diagnostic results of a system that facilitates detection of fuel in oil, lube degradation, and foreign object contamination through optical and/or color characterization in accordance with one or more embodiments described herein.

FIG. 13 illustrates an example, non-limiting graph 1300 of diagnostic results of a system that can facilitate detection of fuel in oil, lube degradation, and foreign object contamination through optical and/or color characterization in accordance with one or more embodiments described herein.

As shown, the graph 1300 depicts illustrative results and/or visualizations that can, in various embodiments, be outputted by the analysis component 118. As explained above, existing systems/techniques for monitoring engine lube in situ generally provide only binary results (e.g., contamination detected or no contamination detected, deterioration detected or no deterioration detected, and so on), or they generally identify only a select few contaminants present in the lubricant 110 (e.g., identifying concentration levels of only metallic ions). Indeed, existing systems/techniques generally identify in piecewise-fashion only certain contaminants (e.g., chemicals that should not be present in the lubricant 110). In stark contrast, various embodiments of the subject claimed innovation can provide far more comprehensive results, such as a substantially full compositional makeup of the lubricant 110 (e.g., identifying levels of chemical contaminants that should not be in the lubricant 110 as well as identifying levels of chemical constituents that should be in the lubricant 110, and so on).

Graph 1300 depicts an example visualization and/or output that can visually illustrate such comprehensive results (e.g., a circular, multi-axis diagram, with each axis representing concentration of a particular chemical and/or family or group of chemicals, where portions of the axes closer to the center of the diagram represent lower levels/concentrations of the chemicals). As shown in FIG. 13, the dotted line can represent concentration level of each chemical listed in the graph 1300. For example, graph 1300 indicates that the lubricant 110 at a particular location exhibited a high coke build-up and high concentrations of amines and silicates (e.g., because the dotted line is closer to the edge of the circle when it intersects the coke axis, the amine axis, and the silicate axis). Graph 1300 also indicates low concentrations/levels of moisture, varnish, deterioration, alkanes, naphthenes, nitrides, sulphides, phenolics, esters, and aromatics (e.g., because the dotted line is closer to the center of the circle when it intersects the moisture, varnish, deterioration, alkane, naphthene, oxide, nitride, sulphide, phenolic, ester, and aromatic axes). In various embodiments, other visualizations to illustrate composition and/or health of the lubricant 110 can be implemented (e.g., bar graphs, pie charts, and so on).

In any case, various embodiments of the subject claimed innovation can output comprehensive composition of the lubricant 110 (e.g., including determined concentration levels of constituents that should be present, such as alkanes, naphthenes, aromatics, and so on, as well as determined concentration levels of contaminants that should not be present, such as coke, fuel, moisture, and so on).

It should be appreciated that FIG. 13 is illustrative and nonlimiting only.

Figure 14:
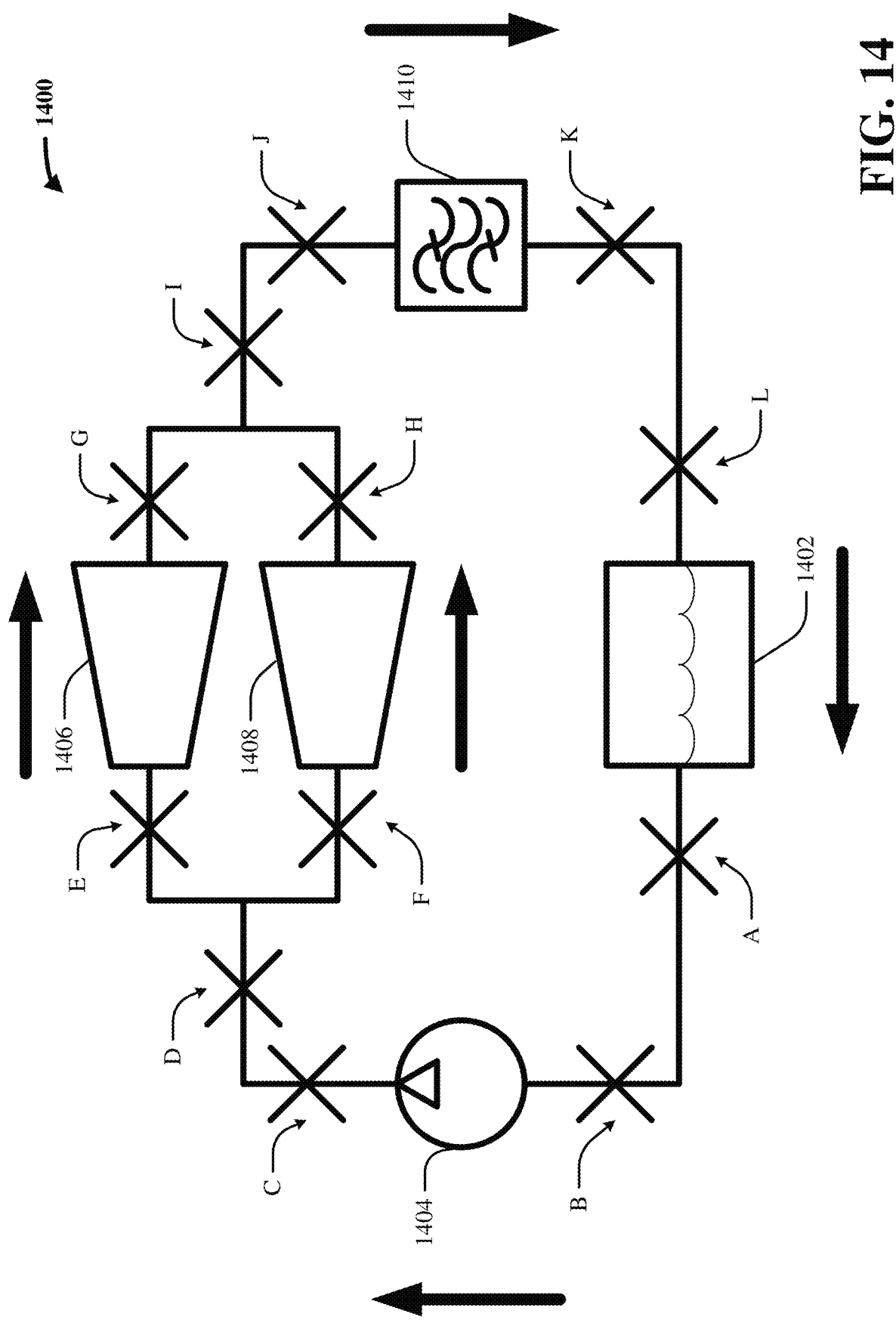
FIG. 14 illustrates a high-level schematic diagram of an example, non-limiting configuration of sensor arrays that facilitates detection of fuel in oil, lube degradation, and foreign object contamination through optical and/or color characterization in accordance with one or more embodiments described herein.

FIG. 14 illustrates a high-level schematic diagram of an example, non-limiting configuration 1400 of sensor arrays that can facilitate detection of fuel in oil, lube degradation, and foreign object contamination through optical and/or color characterization in accordance with one or more embodiments described herein.

As shown, FIG. 14 depicts an illustrative, non-limiting, exemplary configuration of the lubrication circuit 108, comprising an oil tank/sump 1402, an oil pump 1404, a plurality of rotary components 1406 and 1408 (e.g., engine turbines, engine crankshafts, engine bearings, and so on), and an oil filter 1410. In various embodiments, any suitable lubrication circuit components and/or paths can be incorporated. The bolded arrows in FIG. 14 can represent a flow direction of the lubricant 110 through the depicted lubrication circuit 108. The X's (e.g., labeled A-L) can represent locations at which an optical and/or color sensor array is located. In the example shown in FIG. 14, a sensor array is located at the inlet and outlet of each primary component of the lubrication circuit 108. In various embodiments, sensor arrays can be placed in more, fewer, and/or different locations, and can be placed at either regular and/or irregular intervals, and so on.

As explained above, in various embodiments, each sensor array can determine a comprehensive composition and/or health of the lubricant 110 at its corresponding location. Also as mentioned above, the baseline health and/or composition of the lubricant 110 can vary along the lubrication circuit 108 (e.g., different baseline signatures at the different locations A-L).

In various embodiments, the analysis component 118 can leverage a plurality of sensor arrays to determine where repair and/or maintenance efforts should be directed/targeted in the lubrication circuit 108. For example, if the sensor arrays at locations A, F, G, and K each indicate high levels of coking and/or slag, the analysis component 118 can determine that locations A, F, G, and K should be scheduled for coking/slag inspection. In some cases, the analysis component 118 can send out a warning, message, and/or communication to that effect to an operator of the lubrication circuit 108. As another example, if multiple sensors indicate the presence of fuel (or any other contaminant) in the lubricant 110, the analysis component 118 can estimate and/or infer where the fuel entered the lubrication circuit 108, based on the location of the sensor array that was temporally first to detect the fuel. In various cases, the immediately upstream sensor array that did not detect the fuel can be used for disambiguation/targeting purposes. For instance, if the sensor array at location E was the first to detect fuel contamination in the lubricant 110, then the analysis component 118 can determine that the fuel entered the lubrication circuit 108 at some point between location E and location D (e.g., assuming that the fuel did not "sneak" past the sensor array at location D, which the configuration 402 depicted in FIG. 4 can help to prevent). Thus, a warning, message, and/or communication requesting maintenance can be generated that specifically indicates that the pipe/channels between location D and location E should be targeted for maintenance. As another example, if the sensor array at location I is the first to detect a moisture contamination, the analysis component 118 can infer that the moisture entered the lubrication circuit 108 at some point between location G and location I and/or between location H and location I (e.g., again, the assumption can, in some embodiments, be made that the moisture did not "sneak" past the sensor array at location G or location H).

Since existing systems/techniques for engine lube monitoring generally utilize only a single sensor to detect the health of the lubricant, they are unable to provide such specific, targeted inferences and/or recommendations regarding what particular portions of the lubrication circuit 108 require attention.

It should be noted that FIG. 14 is not drawn to scale, is nonlimiting, and is exemplary only.

Figure 15:
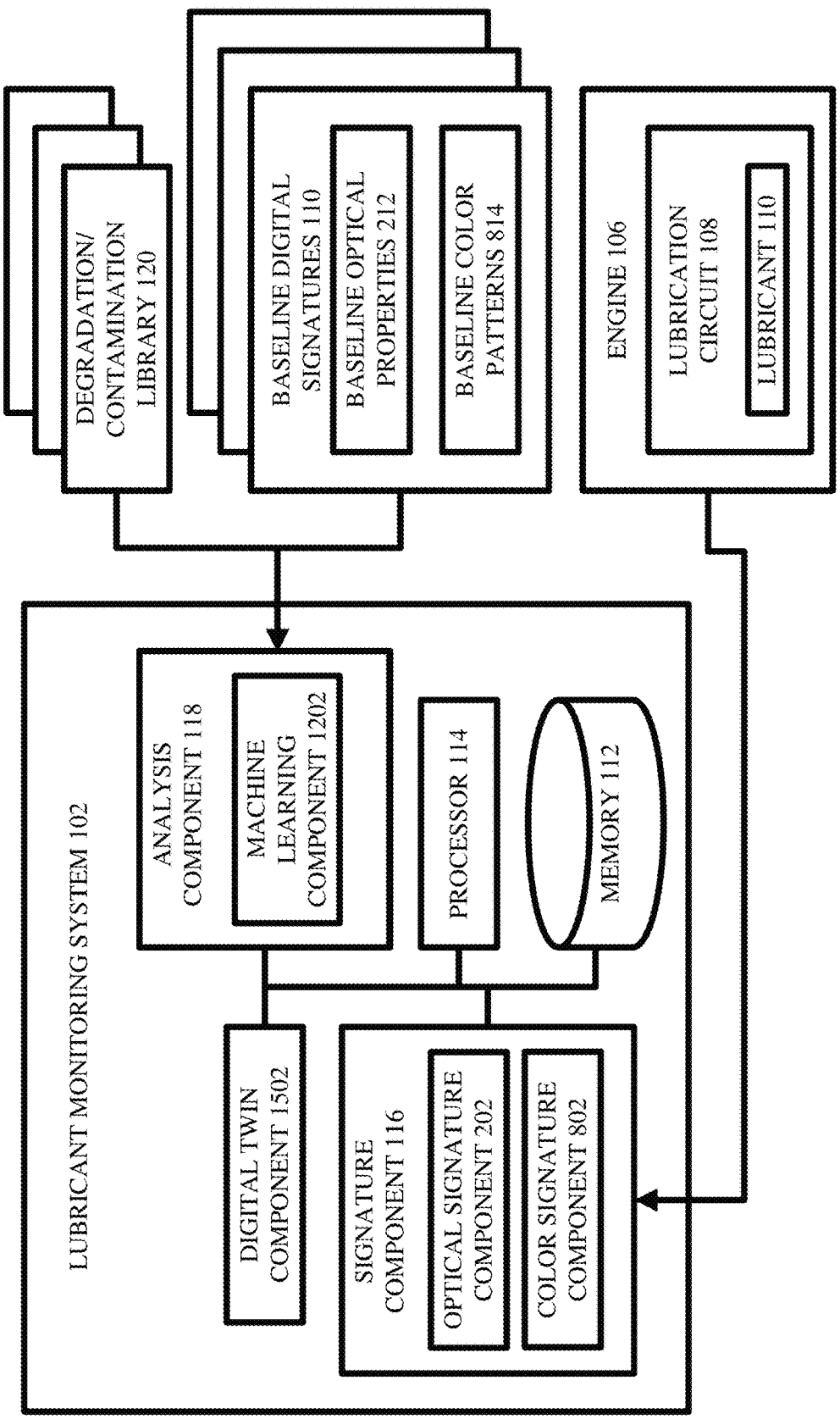
FIG. 15 illustrates a block diagram of an example, non-limiting system including a digital twin component that facilitates detection of fuel in oil, lube degradation, and foreign object contamination through optical and/or color characterization in accordance with one or more embodiments described herein.

FIG. 15 illustrates a block diagram of an example, non-limiting system 1500 including a digital twin component that can facilitate detection of fuel in oil, lube degradation, and foreign object contamination through optical and/or color characterization in accordance with one or more embodiments described herein. As shown, the system 1500 can, in various embodiments, comprise the same components as the system 1200, and can further comprise a digital twin component 1502.

In one or more embodiments, the digital twin component 1502 can monitor performance of the engine 106 (e.g., monitor the results outputted by the analysis component 118, monitor the digital signatures generated by the signature component 116, and so on). In various embodiments, the digital twin component 1502 can recommend corrective, preventative, and/or ameliorative actions to the engine 106 (e.g., to an operator of the engine 106 and/or an operator of the lubrication circuit 108, and so on). In various aspects, a digital twin can be a digital model/representation of a physical entity (e.g., Internet of Things device, and so on) that is subject to the dynamics of the physical entity (e.g., the digital twin can react to stimuli in the same, substantially same, and/or approximately same way as the physical entity would react to the stimuli). A digital twin can allow for potential actions and/or operations of the physical entity to be digitally simulated prior to actual implementation, which can allow for effective cost-benefit analyses of the potential actions/operations and thus for better entity management.

In various embodiments, the digital twin component 1502 can create a digital twin of the lubricant 110 flowing through the lubrication circuit 108. For example, the digital twin component 1502 can generate an analytic and/or computational model of the lubricant 110, such that the model emulates the thermodynamic, fluid dynamic, aerodynamic, structural, and/or vibrational characteristics of the lubricant 110 flowing through the lubrication circuit 108 (e.g., via finite element analysis (FEA), computational fluid dynamics (CFD), and so on). In some aspects, the digital twin component 1502 can continuously, continually, periodically, and/or aperiodically update the digital twin of the lubricant 110 (e.g., sending the results of the analysis component 118 and/or the generated digital signatures to the digital twin). For example, if the analysis component 118 determines that there is a slag/sludge build-up at a first location in the lubrication circuit 108 and that there is a fuel contamination in the lubricant 110 that likely originated from a second location in the lubrication circuit 108, the digital twin component 1502 can update the digital twin of the lubricant 110 to reflect these facts/inferences. Then, digital simulations of the lubricant 110 flowing through the lubrication circuit 108 can take into account such information, and/or automated requests for specific types of maintenance can be made accordingly.

In various embodiments, the digital twin component 1502 can update the digital twin of the lubricant 110 based on results from manual lubrication inspections and/or repairs/servicing. In such cases, the presence of detected coking, slag, varnish, and/or contaminants can be confirmed and/or denied by the manual servicing, and the digital twin can be updated based on whether the inferences/results outputted by the analysis component 118 were correct. If the inferences (e.g., coking detected at a certain location) were correct, the digital twin can be updated to indicate that the machine learning component 1202 employed by the analysis component 118 is functioning properly. If the inferences were incorrect, the digital twin can be updated to indicate that the machine learning component 1202 requires additional training and/or correction (e.g., manual and/or automated adjustment to neural network weights, and so on). In such cases, the digital twin component 1502 can employ a self-learning algorithm that improves the digital twin based on the confirmation or denial of the outputted results. In various embodiments, any suitable self-learning algorithm can be implemented. For example, if the analysis component 118 determines that there is a moderate coke build-up at a particular location in the lubrication circuit 108, but a subsequent manual inspection denies this inference and instead finds a heavy varnish at that location, the digital twin component 1502 can update the digital twin accordingly and can cause a recalibration of the machine learning component 1202 employed by the analysis component 118. In such recalibration, an automated and/or manual adjustment of one or more aspects (e.g., weights, biases, and so on) of the machine learning component 1202 can be performed such that the digital signatures generated by the signature component 116 for that particular location are correlated to a heavy varnish contamination and are no longer correlated with a moderate coking build-up.

Figure 16:
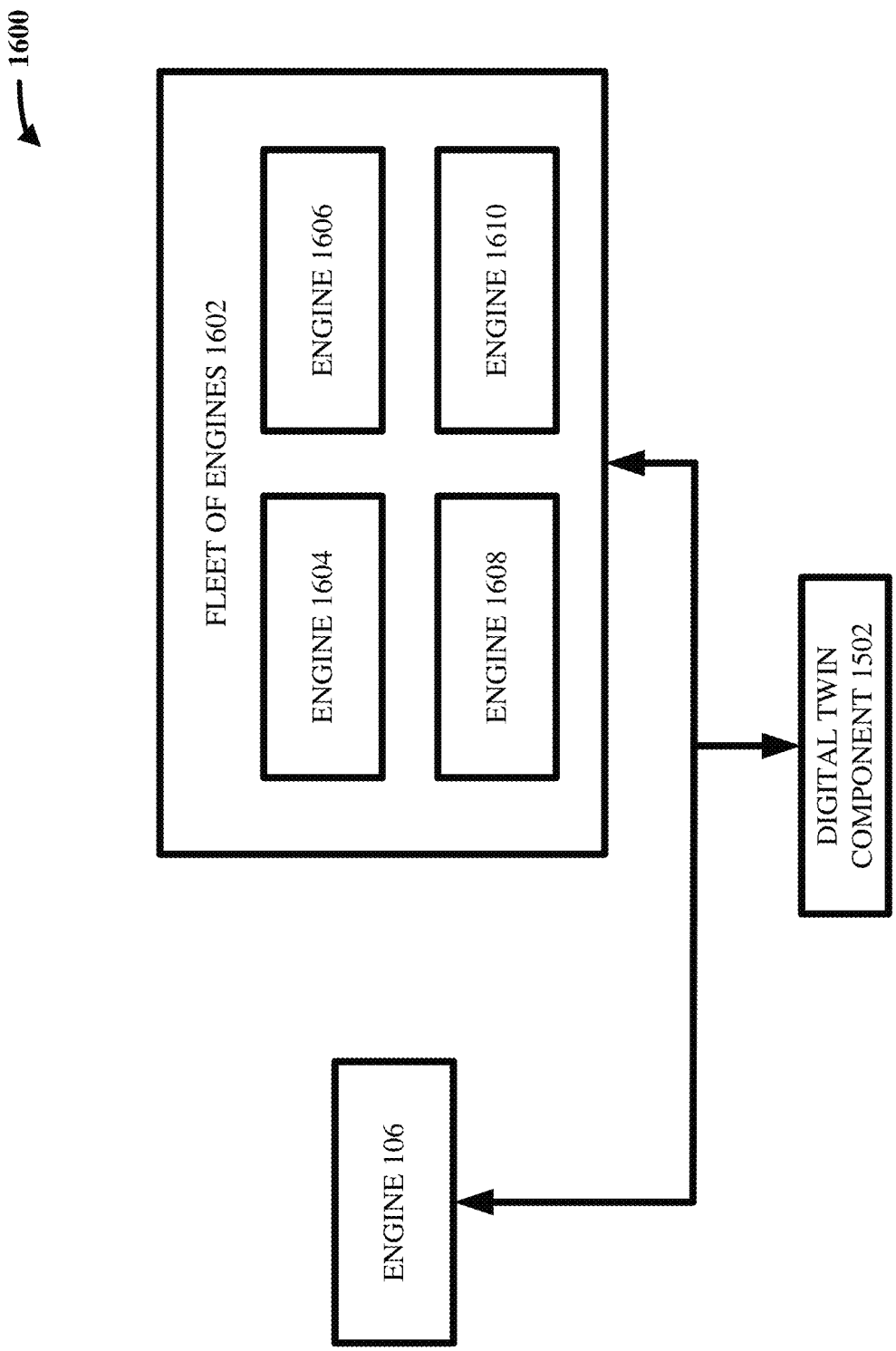
FIG. 16 illustrates a block diagram of an example, non-limiting system including a fleet of engines that facilitates detection of fuel in oil, lube degradation, and foreign object contamination through optical and/or color characterization in accordance with one or more embodiments described herein.

FIG. 16 illustrates a block diagram of an example, non-limiting system 1600 including a fleet of engines that facilitates detection of fuel in oil, lube degradation, and foreign object contamination through optical and/or color characterization in accordance with one or more embodiments described herein.

FIG. 16 depicts one or more embodiments of the subject claimed innovation where the digital twin component 1502 can be communicatively coupled to a fleet of engines 1602 as well as to the engine 106. As shown, the fleet of engines 1602 can comprise one or more other engines (e.g., 1604, 1606, 1608, 1610, and so on). Although only four other engines are depicted, any number of other engines can be in the fleet of engines 1602 in various embodiments. In various aspects, the engine 106 can be considered part of the fleet of engines 1602.

In various instances, the digital twin component 1502 can track emerging trends in the fleet of engines 1602 (e.g., tracking one or more inferences, determinations, and/or digital signatures corresponding to lubricants in lubrication circuits of the engines in the fleet). For example, in various instances, the digital twin can be a global digital twin that represents not just the lubrication circuit 108 of the single engine 106, but also all other lubrication circuits of engines of the same make/model as the engine 106 that are in the fleet of engines 1602. In various aspects, the digital twin component 1502 can update the global digital twin based on inferences, determinations, and/or digital signatures of lubricants from each of the other engines in the fleet of engines 1602 and based on the inferences, determinations, and/or digital signatures of the lubricant 110 from the engine 106. Such a global digital twin can, in various instances, essentially allow for each engine in the fleet of engines 1602 to learn from the mistakes of other engines in the fleet of engines 1602. For instance, as explained above, if an inference/determination of the analysis component 118 for the engine 106 is denied by a subsequent maintenance inspection, the digital twin component 1502 can cause a recalibration/update of the machine learning component 1202 employed by the analysis component 118 based on the denial. In such case where a global digital twin is employed, the same/similar corrective recalibration/update can be simultaneously scheduled and/or performed for all the engines in the fleet of engines 1602 (e.g., such that the entire fleet learned from the mistake of a single engine). Similarly, if an inference/determination of one of the engines in the fleet of engines 1602 is proven incorrect by a subsequent maintenance inspection, the machine learning component 1202 employed by the analysis component 118 corresponding to the engine 106 can be updated/recalibrated accordingly.

The digital twin component 1502 can, in various embodiments, monitor the entire fleet of engines 1602 and can request and/or perform servicing and maintenance as needed. In various embodiments, the digital twin component 1502 can monitor the inferences/determinations from the analysis component 118 of the engine 106 and from corresponding analysis components in the fleet of engines 1602 in search of emerging trends. The recommendations of the digital twin component 1502 and/or the analysis component 118 can be based, in various embodiments, on these emerging trends.

Figure 17:
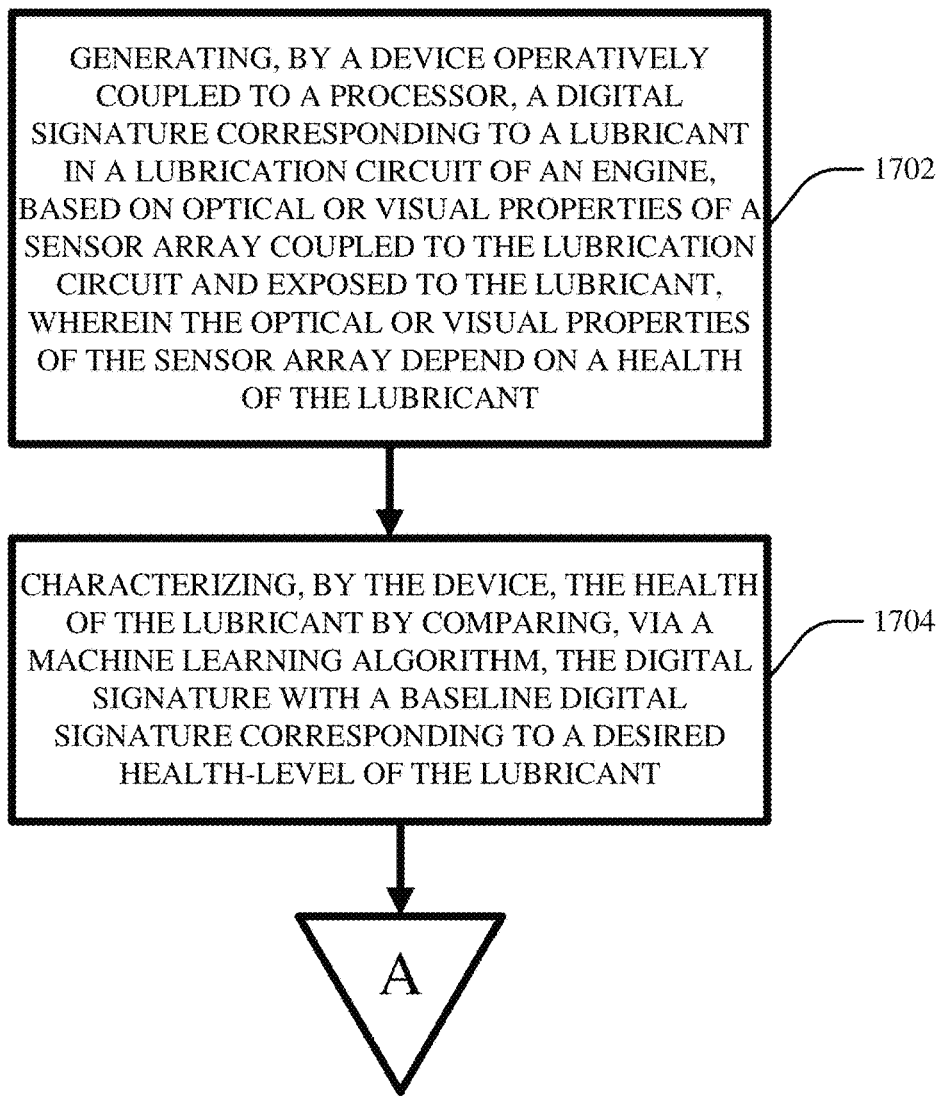
FIG. 17 illustrates a flow diagram of an example, non-limiting computer-implemented method that facilitates detection of fuel in oil, lube degradation, and foreign object contamination through optical and/or color characterization in accordance with one or more embodiments described herein.

FIG. 17 illustrates a flow diagram of an example, non-limiting computer-implemented method 1700 that can facilitate detection of fuel in oil, lube degradation, and foreign object contamination through optical and/or color characterization in accordance with one or more embodiments described herein.

In various embodiments, act 1702 can include generating, by a device operatively coupled to a processor, a digital signature (e.g., via the signature component 116) corresponding to a lubricant (e.g., lubricant 110) in a lubrication circuit (e.g., lubrication circuit 108) of an engine (e.g., engine 106). The digital signature can be based on optical or visual properties (e.g., fluorescence, reflectance, and so on; color, color shade, and so on) of a sensor array (e.g., optical sensor array 204 and/or color sensor array 804) that is coupled to the lubrication circuit (e.g., as shown in FIG. 4) and exposed to the lubricant. In various aspects, the optical or visual properties of the sensor array can depend on a health and/or composition of the lubricant.

In various instances, act 1704 can include characterizing, by the device, the health and/or composition of the lubricant (e.g., via the analysis component 118) by comparing, via a machine learning algorithm (e.g., machine learning component 1202), the digital signature with a baseline digital signature (e.g., baseline digital signatures 104) corresponding to a desired health-level of the lubricant.

Figure 18:
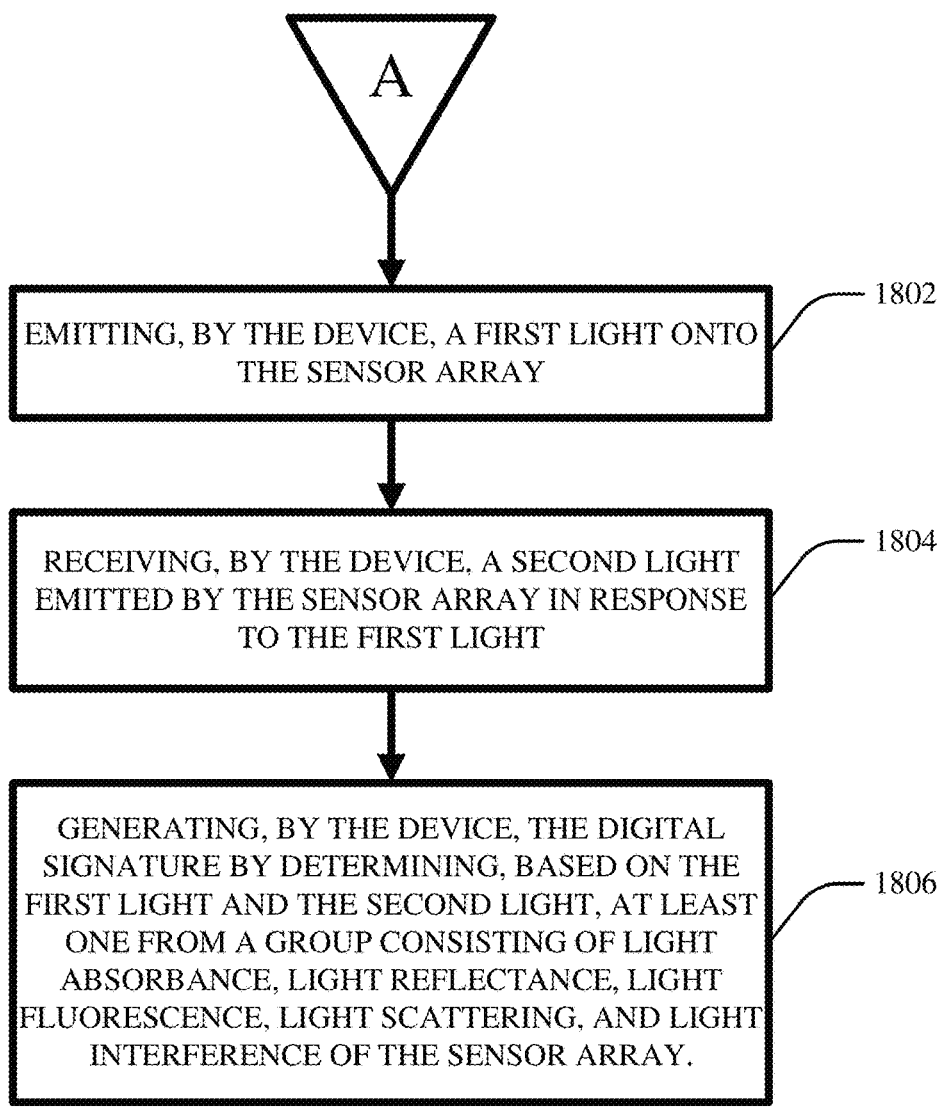
FIG. 18 illustrates a flow diagram of an example, non-limiting computer-implemented method that facilitates detection of fuel in oil, lube degradation, and foreign object contamination through optical characterization in accordance with one or more embodiments described herein.

FIG. 18 illustrates a flow diagram of an example, non-limiting computer-implemented method 1800 that can facilitate detection of fuel in oil, lube degradation, and foreign object contamination through optical characterization in accordance with one or more embodiments described herein. As shown, the computer-implemented method 1800 can, in various embodiments, comprise the same acts as the computer-implemented method 1700, and can further comprise acts 1802, 1804, and 1806.

In various embodiments, act 1802 can include emitting, by the device (e.g., via the light emitting component 206), a first light (e.g., first light 306) onto the sensor array (e.g., optical sensor array 204).

In various instances, act 1804 can include receiving, by the device (e.g., via the light receiving component 208), a second light (e.g., second light 308) emitted by the sensor array in response to the first light.

In various aspects, act 1806 can include generating, by the device (e.g., via the signature component 116), the digital signature by determining (e.g., via the optical signature component 202), based on the first light and the second light, at least one from a group consisting of light absorbance, light reflectance, light fluorescence, light scattering, and light interference of the sensor array.

Figure 19:
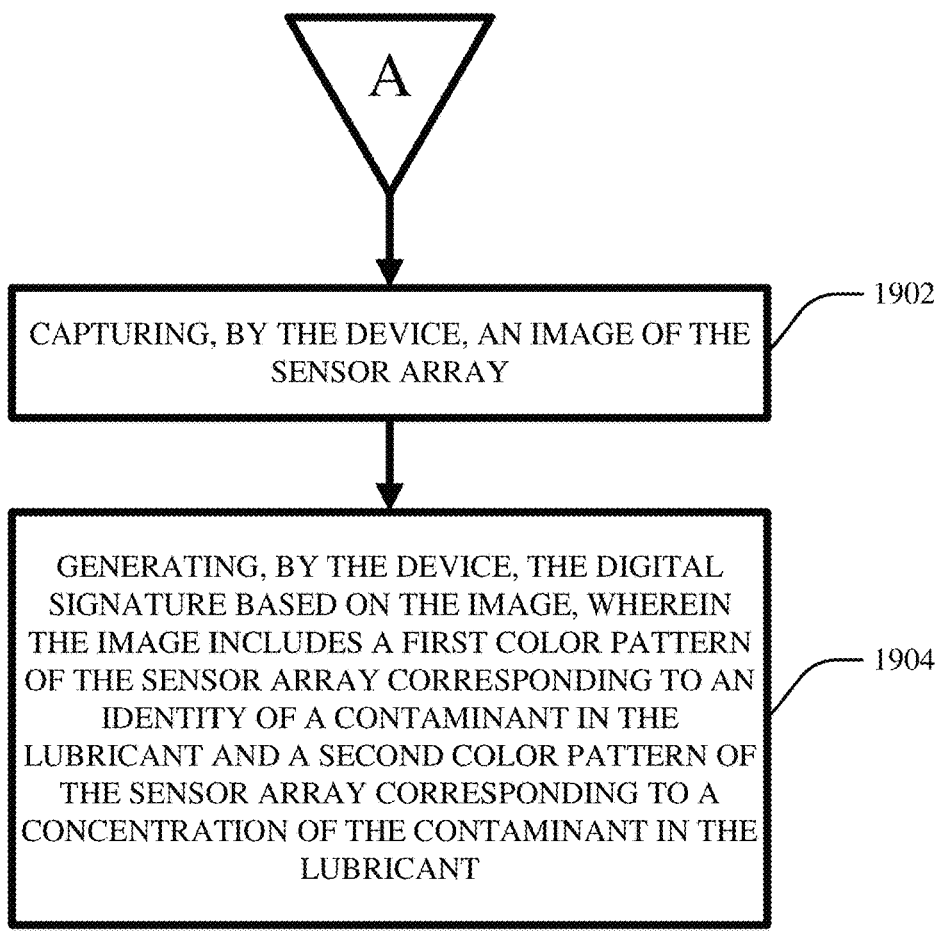
FIG. 19 illustrates a flow diagram of an example, non-limiting computer-implemented method that facilitates detection of fuel in oil, lube degradation, and foreign object contamination through color characterization in accordance with one or more embodiments described herein.

FIG. 19 illustrates a flow diagram of an example, non-limiting computer-implemented method 1900 that can facilitate detection of fuel in oil, lube degradation, and foreign object contamination through color characterization in accordance with one or more embodiments described herein. As shown, the computer-implemented method 1900 can, in various embodiments, comprise the same acts as the computer-implemented method 1700, and can further comprise acts 1902 and 1904.

In various embodiments, act 1902 can include capturing, by the device (e.g., via image capture component 810), an image of the sensor array (e.g., color sensor array 804).

In various instances, act 1904 can include generating, by the device (e.g., via the signature component 116), the digital signature based on the image, wherein the image includes a first color pattern of the sensor array corresponding to an identity of a contaminant in the lubricant (e.g., color pattern exhibited by one or more dye strips 806) and a second color pattern of the sensor array corresponding to a concentration of the contaminant in the lubricant (e.g., color pattern exhibited by one or more pH strips 808).

Various aspects of the subject claimed innovation have never been implemented in a variety of contexts/fields, including the aerospace industry.

Figure 20:
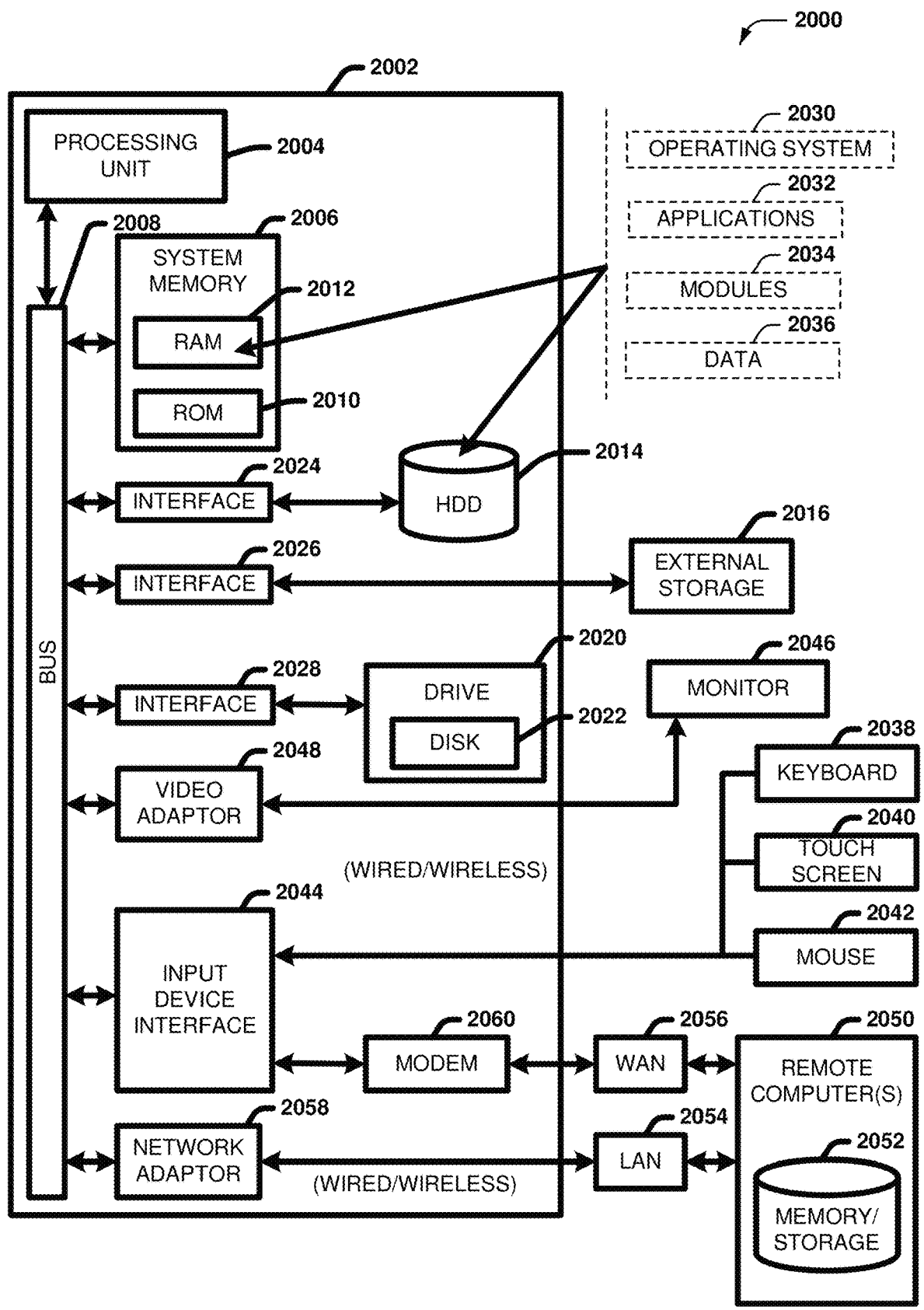
FIG. 20 illustrates a block diagram of an example, non-limiting operating environment in which one or more embodiments described herein can be facilitated.

In order to provide additional context for various embodiments described herein, FIG. 20 and the following discussion are intended to provide a brief, general description of a suitable computing environment 2000 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 20, the example environment 2000 for implementing various embodiments of the aspects described herein includes a computer 2002, the computer 2002 including a processing unit 2004, a system memory 2006 and a system bus 2008. The system bus 2008 couples system components including, but not limited to, the system memory 2006 to the processing unit 2004. The processing unit 2004 can be any of various commercially available processors. Dual microprocessors and other multi-processor architectures can also be employed as the processing unit 2004.

The system bus 2008 can be any of several types of bus structure that can further interconnect to a memory bus (with or without a memory controller), a peripheral bus, and a local bus using any of a variety of commercially available bus architectures. The system memory 2006 includes ROM 2010 and RAM 2012. A basic input/output system (BIOS) can be stored in a non-volatile memory such as ROM, erasable programmable read only memory (EPROM), EEPROM, which BIOS contains the basic routines that help to transfer information between elements within the computer 2002, such as during startup. The RAM 2012 can also include a high-speed RAM such as static RAM for caching data.

The computer 2002 further includes an internal hard disk drive (HDD) 2014 (e.g., EIDE, SATA), one or more external storage devices 2016 (e.g., a magnetic floppy disk drive (FDD) 2016, a memory stick or flash drive reader, a memory card reader, etc.) and a drive 2020, e.g., such as a solid state drive, an optical disk drive, which can read or write from a disk 2022, such as a CD-ROM disc, a DVD, a BD, etc. Alternatively, where a solid state drive is involved, disk 2022 would not be included, unless separate. While the internal HDD 2014 is illustrated as located within the computer 2002, the internal HDD 2014 can also be configured for external use in a suitable chassis (not shown). Additionally, while not shown in environment 2000, a solid state drive (SSD) could be used in addition to, or in place of, an HDD 2014. The HDD 2014, external storage device(s) 2016 and drive 2020 can be connected to the system bus 2008 by an HDD interface 2024, an external storage interface 2026 and a drive interface 2028, respectively. The interface 2024 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2002, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2012, including an operating system 2030, one or more application programs 2032, other program modules 2034 and program data 2036. All or portions of the operating system, applications, modules, and/or data can also be cached in the RAM 2012. The systems and methods described herein can be implemented utilizing various commercially available operating systems or combinations of operating systems.

Computer 2002 can optionally comprise emulation technologies. For example, a hypervisor (not shown) or other intermediary can emulate a hardware environment for operating system 2030, and the emulated hardware can optionally be different from the hardware illustrated in FIG. 20. In such an embodiment, operating system 2030 can comprise one virtual machine (VM) of multiple VMs hosted at computer 2002. Furthermore, operating system 2030 can provide runtime environments, such as the Java runtime environment or the .NET framework, for applications 2032. Runtime environments are consistent execution environments that allow applications 2032 to run on any operating system that includes the runtime environment. Similarly, operating system 2030 can support containers, and applications 2032 can be in the form of containers, which are lightweight, standalone, executable packages of software that include, e.g., code, runtime, system tools, system libraries and settings for an application.

Further, computer 2002 can be enabled with a security module, such as a trusted processing module (TPM). For instance with a TPM, boot components hash next in time boot components, and wait for a match of results to secured values, before loading a next boot component. This process can take place at any layer in the code execution stack of computer 2002, e.g., applied at the application execution level or at the operating system (OS) kernel level, thereby enabling security at any level of code execution.

A user can enter commands and information into the computer 2002 through one or more wired/wireless input devices, e.g., a keyboard 2038, a touch screen 2040, and a pointing device, such as a mouse 2042. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2004 through an input device interface 2044 that can be coupled to the system bus 2008, but can be connected by other interfaces, such as a parallel port, an IEEE 1394 serial port, a game port, a USB port, an IR interface, a BLUETOOTH® interface, etc.

A monitor 2046 or other type of display device can be also connected to the system bus 2008 via an interface, such as a video adapter 2048. In addition to the monitor 2046, a computer typically includes other peripheral output devices (not shown), such as speakers, printers, etc.

The computer 2002 can operate in a networked environment using logical connections via wired and/or wireless communications to one or more remote computers, such as a remote computer(s) 2050. The remote computer(s) 2050 can be a workstation, a server computer, a router, a personal computer, portable computer, microprocessor-based entertainment appliance, a peer device or other common network node, and typically includes many or all of the elements described relative to the computer 2002, although, for purposes of brevity, only a memory/storage device 2052 is illustrated. The logical connections depicted include wired/wireless connectivity to a local area network (LAN) 2054 and/or larger networks, e.g., a wide area network (WAN) 2056. Such LAN and WAN networking environments are commonplace in offices and companies, and facilitate enterprise-wide computer networks, such as intranets, all of which can connect to a global communications network, e.g., the Internet.

When used in a LAN networking environment, the computer 2002 can be connected to the local network 2054 through a wired and/or wireless communication network interface or adapter 2058. The adapter 2058 can facilitate wired or wireless communication to the LAN 2054, which can also include a wireless access point (AP) disposed thereon for communicating with the adapter 2058 in a wireless mode.

When used in a WAN networking environment, the computer 2002 can include a modem 2060 or can be connected to a communications server on the WAN 2056 via other means for establishing communications over the WAN 2056, such as by way of the Internet. The modem 2060, which can be internal or external and a wired or wireless device, can be connected to the system bus 2008 via the input device interface 2044. In a networked environment, program modules depicted relative to the computer 2002 or portions thereof, can be stored in the remote memory/storage device 2052. It will be appreciated that the network connections shown are example and other means of establishing a communications link between the computers can be used.

When used in either a LAN or WAN networking environment, the computer 2002 can access cloud storage systems or other network-based storage systems in addition to, or in place of, external storage devices 2016 as described above, such as but not limited to a network virtual machine providing one or more aspects of storage or processing of information. Generally, a connection between the computer 2002 and a cloud storage system can be established over a LAN 2054 or WAN 2056 e.g., by the adapter 2058 or modem 2060, respectively. Upon connecting the computer 2002 to an associated cloud storage system, the external storage interface 2026 can, with the aid of the adapter 2058 and/or modem 2060, manage storage provided by the cloud storage system as it would other types of external storage. For instance, the external storage interface 2026 can be configured to provide access to cloud storage sources as if those sources were physically connected to the computer 2002.

The computer 2002 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further aspects of various embodiments of the subject claimed innovation are provided by the subject matter of the following clauses:

1. A system, comprising: a memory that stores computer-executable components; and a processor, operably coupled to the memory, that executes the computer-executable components stored in the memory, wherein the computer-executable components comprise: a signature component that generates a digital signature corresponding to a lubricant in a lubrication circuit of an engine, based on optical or visual properties of a sensor array coupled to the lubrication circuit and exposed to the lubricant, wherein the optical or visual properties of the sensor array depend on a health of the lubricant; and an analysis component that characterizes the health of the lubricant by comparing, via a machine learning algorithm, the digital signature with a baseline digital signature corresponding to a desired health-level of the lubricant.

2. The system of any preceding clause wherein the computer-executable components further comprise: a light emitter component that emits a first light onto the sensor array; and a light receiver component that receives a second light emitted by the sensor array in response to the first light; wherein the signature component generates the digital signature by determining, based on the first light and the second light, at least one from a group consisting of light absorbance, light reflectance, light fluorescence, light scattering, and light interference of the sensor array.

3. The system of any preceding clause wherein the first light is one from a group consisting of infrared light, ultraviolet light, blue light, and multi-laser light inputs of different wavelengths.

4. The system of any preceding clause wherein the sensor array comprises one from a group consisting of a ring array of chemo-responsive optical coatings with each coating of the ring array wrapping radially around an inner surface of a channel of the lubrication circuit and a parallel array of chemo-responsive optical coatings with each coating of the parallel array extending longitudinally along an inner surface of a channel of the lubrication circuit.

5. The system of any preceding clause wherein the computer-executable components further comprise: an image capture component that captures an image of the sensor array; wherein the signature component generates the digital signature based on the image, and wherein the image includes a first color pattern of the sensor array corresponding to an identity of a contaminant in the lubricant and a second color pattern of the sensor array corresponding to a concentration of the contaminant in the lubricant.

6. The system of any preceding clause wherein the sensor array comprises a chemical dye strip that exhibits the first color pattern based on being exposed to the contaminant in the lubricant, and wherein the sensor array further comprises a gradient-based pH dye strip that exhibits the second color pattern based on being exposed to the contaminant in the lubricant.

7. The system of any preceding clause wherein the health of the lubricant includes at least one from a group consisting of a deterioration level of the lubricant, an identity of a contaminant in the lubricant, and a concentration of a contaminant in the lubricant.

8. A computer-implemented method, comprising: generating, by a device operatively coupled to a processor, a digital signature corresponding to a lubricant in a lubrication circuit of an engine, based on optical or visual properties of a sensor array coupled to the lubrication circuit and exposed to the lubricant, wherein the optical or visual properties of the sensor array depend on a health of the lubricant; and characterizing, by the device, the health of the lubricant by comparing, via a machine learning algorithm, the digital signature with a baseline digital signature corresponding to a desired health-level of the lubricant.

9. The computer-implemented method of any preceding clause further comprising: emitting, by the device, a first light onto the sensor array; receiving, by the device, a second light emitted by the sensor array in response to the first light; and generating, by the device, the digital signature by determining, based on the first light and the second light, at least one from a group consisting of light absorbance, light reflectance, light fluorescence, light scattering, and light interference of the sensor array.

10. The computer-implemented method of any preceding clause wherein the first light is one from a group consisting of infrared light, ultraviolet light, blue light, and multi-laser light inputs of different wavelengths.

11. The computer-implemented method of any preceding clause wherein the sensor array comprises one from a group consisting of a ring array of chemo-responsive optical coatings with each coating of the ring array wrapping radially around an inner surface of a channel of the lubrication circuit and a parallel array of chemo-responsive optical coatings with each coating of the parallel array extending longitudinally along an inner surface of a channel of the lubrication circuit.

12. The computer-implemented method of any preceding clause further comprising: capturing, by the device, an image of the sensor array; and generating, by the device, the digital signature based on the image, wherein the image includes a first color pattern of the sensor array corresponding to an identity of a contaminant in the lubricant and a second color pattern of the sensor array corresponding to a concentration of the contaminant in the lubricant.

13. The computer-implemented method of any preceding clause wherein the sensor array comprises a chemical dye strip that exhibits the first color pattern based on being exposed to the contaminant in the lubricant, and wherein the sensor array further comprises a gradient-based pH dye strip that exhibits the second color pattern based on being exposed to the contaminant in the lubricant.

14. The computer-implemented method of any preceding clause wherein the health of the lubricant includes at least one from a group consisting of a deterioration level of the lubricant, an identity of a contaminant in the lubricant, and a concentration of a contaminant in the lubricant.

15. A computer program product for facilitating detection of fuel in oil, lube degradation, and foreign object contamination through optical characterization, the computer program product comprising a computer readable memory having program instructions embodied therewith, the program instructions executable by a processing component to cause the processing component to: generate a digital signature corresponding to a lubricant in a lubrication circuit of an engine, based on optical or visual properties of a sensor array coupled to the lubrication circuit and exposed to the lubricant, wherein the optical or visual properties of the sensor array depend on a health of the lubricant; and characterize the health of the lubricant by comparing, via a machine learning algorithm, the digital signature with a baseline digital signature corresponding to a desired health-level of the lubricant.

16. The computer program product of any preceding claim wherein the program instructions are further executable to cause the processing component to: emit a first light onto the sensor array; receive a second light emitted by the sensor array in response to the first light; and generate the digital signature by determining, based on the first light and the second light, at least one from a group consisting of light absorbance, light reflectance, light fluorescence, light scattering, and light interference of the sensor array.

17. The computer program product of any preceding clause wherein the first light is one from a group consisting of infrared light, ultraviolet light, blue light, and multi-laser light inputs of different wavelengths.

18. The computer program product of any preceding clause wherein the sensor array comprises one from a group consisting of a ring array of chemo-responsive optical coatings with each coating of the ring array wrapping radially around an inner surface of a channel of the lubrication circuit and a parallel array of chemo-responsive optical coatings with each coating of the parallel array extending longitudinally along an inner surface of a channel of the lubrication circuit.

19. The computer program product of any preceding clause wherein the program instructions are further executable to cause the processing component to: capture an image of the sensor array; and generate the digital signature based on the image, wherein the image includes a first color pattern of the sensor array corresponding to an identity of a contaminant in the lubricant and a second color pattern of the sensor array corresponding to a concentration of the contaminant in the lubricant.

20. The computer program product of any preceding clause wherein the sensor array comprises a chemical dye strip that exhibits the first color pattern based on being exposed to the contaminant in the lubricant, and wherein the sensor array further comprises a gradient-based pH dye strip that exhibits the second color pattern based on being exposed to the contaminant in the lubricant.

What is claimed is:

1. A system that characterizes health of a lubricant circulating in a lubrication circuit of an engine, the system comprising:
   one or more processors; and
   a memory storing instructions that, when executed by the one or more processors, cause the system to function as:
     a sensor array coupled to the lubrication circuit in the engine, the sensor array providing optical or visual properties that depend on the health of the lubricant, and the sensor array producing a sensor array output;
     a signature component that receives the sensor array output and generates a digital signature; and
     an analysis component that receives the digital signature generated by the signature component and that compares, via a machine learning algorithm, the digital signature with a baseline digital signature corresponding to a desired health-level of the lubricant, in order to characterize the health of the lubricant, the analysis component outputting a value representing the health of the lubricant.

2. The system of claim 1, wherein the system further functions as a display that receives and outputs the value representing the health of the lubricant.

3. The system of claim 1, wherein the health of the lubricant includes at least one from a group consisting of a deterioration level of the lubricant, an identity of a contaminant in the lubricant, and a concentration of a contaminant in the lubricant.

4. The system of claim 1, wherein the system further functions as:
   a light emitting component that emits a first light onto the sensor array; and
   a light receiving component that receives a second light emitted by the sensor array in response to the first light, wherein the signature component generates the digital signature by determining, based on the first light and the second light, at least one from a group consisting of light absorbance, light reflectance, light fluorescence, light scattering, and light interference of the sensor array.

5. The system of claim 4, wherein the sensor array comprises one from a group consisting of a ring array of chemo-responsive optical coatings with each coating of the ring array wrapping radially around an inner surface of a channel of the lubrication circuit and a parallel array of chemo-responsive optical coatings with each coating of the parallel array extending longitudinally along an inner surface of a channel of the lubrication circuit.

6. The system of claim 1, wherein the system further functions as an image capture component that captures an image produced by the sensor array, and
   wherein the signature component generates the digital signature based on the image, the image including a first color pattern produced by the sensor array corresponding to an identity of a contaminant in the lubricant and a second color pattern produced by the sensor array corresponding to a concentration of the contaminant in the lubricant.

7. The system of claim 6, wherein the sensor array comprises a chemical dye strip that exhibits the first color pattern based on being exposed to the contaminant in the lubricant, and the sensor array further comprises a gradient-based pH dye strip that exhibits the second color pattern based on being exposed to the contaminant in the lubricant.

8. A computer-implemented method for a system that characterizes health of a lubricant circulating in a lubrication circuit of an engine, the method comprising:
   providing one or more processors; and
   providing a memory storing instructions that, when executed by the one or more processors, cause the system to function by:
     providing, by a sensor array coupled to the lubrication circuit in the engine, optical or visual properties that depend on the health of the lubricant, the sensor array producing a sensor array output;
     receiving, by a signature component, the sensor array output and generating a digital signature; and
     receiving, by an analysis component, the digital signature generated by the signature component and comparing, via a machine learning algorithm, the digital signature with a baseline digital signature corresponding to a desired health-level of the lubricant, in order to characterize the health of the lubricant, the analysis component outputting a value representing the health of the lubricant.

9. The computer-implemented method of claim 8, further causing the system to function by receiving and outputting, by a display, the value representing the health of the lubricant.

10. The computer-implemented method of claim 8, wherein the health of the lubricant includes at least one from a group consisting of a deterioration level of the lubricant, an identity of a contaminant in the lubricant, and a concentration of a contaminant in the lubricant.

11. The computer-implemented method of claim 8, further causing the system to function by:
   emitting, by a light emitting component, a first light onto the sensor array; and
   receiving, by a light receiving component, a second light emitted by the sensor array in response to the first light, wherein the one or more processors generate the digital signature by determining, based on the first light and the second light, at least one from a group consisting of light absorbance, light reflectance, light fluorescence, light scattering, and light interference of the sensor array.

12. The computer-implemented method of claim 11, wherein the sensor array comprises one from a group consisting of a ring array of chemo-responsive optical coatings with each coating of the ring array wrapping radially around an inner surface of a channel of the lubrication circuit and a parallel array of chemo-responsive optical coatings with each coating of the parallel array extending longitudinally along an inner surface of a channel of the lubrication circuit.

13. The computer-implemented method of claim 8, further causing the system to function by capturing, by an image capture component, an image produced by the sensor array,
wherein the one or more processors generate the digital signature based on the image, the image including a first color pattern of the sensor array corresponding to an identity of a contaminant in the lubricant and a second color pattern of the sensor array corresponding to a concentration of the contaminant in the lubricant.

14. The computer-implemented method of claim 13, wherein the sensor array comprises a chemical dye strip that exhibits the first color pattern based on being exposed to the contaminant in the lubricant, and the sensor array further comprises a gradient-based pH dye strip that exhibits the second color pattern based on being exposed to the contaminant in the lubricant.

15. A non-transitory computer readable medium that stores a program for a system that characterizes health of a lubricant circulating in a lubrication circuit of an engine, the program causing a computer to execute:
providing, by a sensor array coupled to the lubrication circuit in the engine, optical or visual properties that depend on the health of the lubricant, the sensor array producing a sensor array output;
receiving, by a signature component, the sensor array output and generating a digital signature; and
receiving, by an analysis component, the digital signature generated by the signature component and comparing, via a machine learning algorithm, the digital signature with a baseline digital signature corresponding to a desired health-level of the lubricant, in order to characterize the health of the lubricant, the analysis component outputting a value representing the health of the lubricant.

16. The program of claim 15, further causing the computer to execute receiving and outputting, by a display, the value representing the health of the lubricant.

17. The program of claim 15, further causing the computer to execute:
causing a light emitting component to emit a first light onto the sensor array;
receiving by a light receiving component, a second light emitted by the sensor array in response to the first light; and
generating the digital signature by determining, based on the first light and the second light, at least one from a group consisting of light absorbance, light reflectance, light fluorescence, light scattering, and light interference of the sensor array.

18. The program of claim 17, wherein the sensor array comprises one from a group consisting of a ring array of chemo-responsive optical coatings, with each coating of the ring array wrapping radially around an inner surface of a channel of the lubrication circuit, and a parallel array of chemo-responsive optical coatings, with each coating of the parallel array extending longitudinally along an inner surface of a channel of the lubrication circuit.

19. The program of claim 15, further causing the computer to execute:
capturing an image produced by the sensor array; and
generating the digital signature based on the image, the image including a first color pattern of the sensor array corresponding to an identity of a contaminant in the lubricant and a second color pattern of the sensor array corresponding to a concentration of the contaminant in the lubricant.

20. The program of claim 19, wherein the sensor array comprises a chemical dye strip that exhibits the first color pattern based on being exposed to the contaminant in the lubricant, and the sensor array further comprises a gradient-based pH dye strip that exhibits the second color pattern based on being exposed to the contaminant in the lubricant.

* * * * *